(12) United States Patent
Kelly et al.

(10) Patent No.: US 7,895,899 B2
(45) Date of Patent: Mar. 1, 2011

(54) MULTI-AXIS, PROGRAMMABLE SPINE TESTING SYSTEM

(76) Inventors: Brian P. Kelly, Bartlett, TN (US); Denis J. DiAngelo, Germantown, TN (US)

( * ) Notice: Subject to any disclaimer, the term of this patent is extended or adjusted under 35 U.S.C. 154(b) by 1092 days.

(21) Appl. No.: 11/607,226

(22) Filed: Dec. 1, 2006

(65) Prior Publication Data

US 2007/0161872 A1     Jul. 12, 2007

Related U.S. Application Data

(60) Provisional application No. 60/741,723, filed on Dec. 3, 2005.

(51) Int. Cl.
*G01B 5/30* (2006.01)
(52) U.S. Cl. .............................. 73/760; 73/774
(58) Field of Classification Search .............. 73/760–860
See application file for complete search history.

(56) References Cited

U.S. PATENT DOCUMENTS

| | | | |
|---|---|---|---|
| 5,337,758 A | 8/1994 | Moore et al. | |
| 6,058,784 A * | 5/2000 | Carroll et al. | 73/856 |
| 6,159,168 A | 12/2000 | Warner et al. | |
| 6,223,604 B1 * | 5/2001 | Fronczak et al. | 73/856 |
| 6,539,328 B1 | 3/2003 | Cremonese et al. | |
| 6,598,486 B2 | 7/2003 | Vilendrer et al. | |
| 6,834,436 B2 | 12/2004 | Townsend et al. | |
| 6,837,892 B2 | 1/2005 | Shoham | |
| 6,865,954 B2 | 3/2005 | Zubok et al. | |
| 6,997,882 B1 | 2/2006 | Parker et al. | |
| 7,040,177 B2 | 5/2006 | Zubok et al. | |
| 7,543,779 B1 * | 6/2009 | Lewis et al. | 244/172.4 |
| 2005/0278157 A1 | 12/2005 | Raschke | |
| 2006/0117864 A1 | 6/2006 | Zubok et al. | |
| 2006/0272424 A1 | 12/2006 | Zubok et al. | |

OTHER PUBLICATIONS

Robodocs, Memphis Business Quarterly, p. 1, 16-19 (Spring 2008).
http://www.instron.us/wa/applications/biomedical/orthopaedic/spine_simulation.aspx? ref=http://www.google.com/search ("Biopuls Multi-Axial Spine Testing System").
http://www.bose-electroforce.com/product.cfm?pid=36&sid=3 ("Multi-Axis Six Degree-of-Freedom Kinematic Spine Simulator").
http://www.bose.com/controller?event=VIEW_STATIC_PAGE_EVENT&url=/enduratec/index.jsp&ck=0 ("About the Electroforce Systems Group").

(Continued)

*Primary Examiner* — Max Noori
(74) *Attorney, Agent, or Firm* — Peter L. Brewer; Baker, Donelson, Bearman, Cadlwell & Berkowitz, PC

(57) ABSTRACT

A biomechanical system for testing a coupled joint is provided. The coupled joint has a fixed first end and a moving second end within the testing system. The testing system includes a servo actuation system operatively connected to the moving end. The system is able to impart at least four degrees of freedom to the moving end of the coupled joint. The testing system also includes a first force sensor disposed between the servo actuation system and the moving end of the coupled joint for sensing applied load, and a second force sensor disposed at the fixed end of the coupled joint for sensing transmitted load. The system also includes a controller for selectively directing input signals to the servo actuation system in order to apply selected forces and/or motions to the moving end of the coupled joint. The coupled joint may be a cervical spine specimen.

36 Claims, 14 Drawing Sheets

OTHER PUBLICATIONS http://www.purdue.edu/UNS/html4ever/2005/050720.Hillberry.spine.html (Venere, Emil, "Machines, software model helping to create better spinal implants"; Jul. 20, 2005).

http://www.simsol.co.uk/spine.shtml ("Spinal Biomedical Fatigue Simulator, Medical simulation joint testing").

http://www.mts.com/en/Bio/news/DEV_002526 (Walsh, Elizabeth; "MTS Introduces Bionix Spine Wear Simulator"; Mar. 21, 2006.).

http://www.mc.vanderbilt.edu/ortho/biomech.html (Vanderbilt Orthopaedic Institute—Biomechanics, Lab Resources, Software Support, Development Support, and Contact Us).

Jansen, Thomas H. and DiAngelo, Denis J., Ph.D., Computer Simulation Studies of Cervical Spine Extension Mechanics; Biomedical Engineering Conference 1997, Apr. 1997; p. 74-76.

DiAngelo, Denis J., Ph.D., and Foley, Kevin T., M.D., An Improved biomedical testing protocol for evaluating spinal . . . ; Neurosurfical Focus Magazine, vol. 17 (Sep. 2004).

MTS Systems Corporation, "New Accessories Expand 'Bio' Testing Capabilities", 2006.

Faber, H.B., et al.; Development of an Experimental Testing Protocol to Study Cervical Spine Mechanics, Biomedical Engineering Conf., Apr. 1997, p. 323-326. (Abstract only).

DiAngelo, Denis J., et al.; Biomedical Testing of an Artificial Cervical Joint and an Anterior Cervical Plate, Journal of Spinal Disorders & Techniq, Aug. 2003. (Abstract only).

Wigfield, Crispin C., et al.; Internal Stress Distribution in Cervical Intervertebral Discs: The Influence of an Artificial Cervical Joint; Oct. 2003. (Abstract only).

Mejia, L., et al.; Design Considerations for a Multi-DOF Kinematic Spine Simulator; European Cells and Materials, vol. 10 Suppl. 3, 2005 (p. 65).

MTS Systems Corporation, "Achieve Testing Certainty with the New MTS Bionix® Spine Wear Simulator", 2006. (4 pages).

E. H. Ledet, et al., "Direct Real-Time Measurement of In Vivo Forces in the Lumbar Spine", The Spine Journal, vol. 5, pp. 85-94 (2005).

C. L. Wigfield, et al., "Internal Stress Distribution in Cervical Discs (The Influence of an Artificial Cervical Joint and Simulated Anterior Interbody Fusion)", Journal of Spinal Disorders & Techniques, vol. 15, No. 5, pp. 441-449 (2003).

D. J. Diangelo, et al., "Bio Mechanical Testing of An Artificial Cervical Joint and An Anterior Cervical Plate", Journal of Spinal Disorders & Techniques, vol. 16, No. 4, pp. 314-323 (2003).

T. H. Jansen, et al, "Computer Simulation Studies at Cervical Spine Exterior Mechanics", Biomedical Engineering Conference, pp. 74-76 (Apr. 4-6, 1997).

H. B. Faber, et al., "Development of an Experimental testing Protocol to Study Cervical Spine Mechanics", Biomedical Engineering Conference, pp. 323-326 (Apr. 4-6, 1997).

Brochure for Biopulse Multi-Axial Spine Testing System, manufactured by Instron Corp. (2005).

Brochure for MTS Systems Corporation entitled "New Accessories Expand 'Bio' Testing Capabilities", (2005) (probably available as far back as 2000).

Article from MTS Systems Corporation entitled "MTS Bionix Testing Solutions" (Sep. 2006).

Brochure from EnduraTEC entitled "New Full Spine Simulator Provides Unique Benefits for Spinal Devices Engineering" (approximately 2003) [EnduraTEC has been bought out by Bose Corp.].

Brochure from Test Resources, Inc. entitled "Spine Test Applications," obtained from www.testresources.com (about 2005).

PCT International Search Report dated Oct. 18, 2007 in International Application No. PCT/US2007/02269.

Written Opinion of the International Searching Authority in PCT/US2007/02269.

* cited by examiner

MULTI-AXIS, PROGRAMMABLE SPINE TESTING SYSTEM

STATEMENT OF RELATED APPLICATIONS

The present application claims priority to a provisional patent application having Ser. No. 60/741,723. That application was filed on Dec. 3, 2005, and is entitled "System and Method for Robotic In Vitro Testing." The provisional application is incorporated herein by reference in its entirety.

BACKGROUND OF THE INVENTION

1. Field of the Invention

The present invention relates to testing systems for coupled joints. More specifically, the invention relates to a biomechanical system that can controllably test portions of a human spine or other coupled joints along multiple axes and degrees of freedom.

2. Description of the Related Art

The spinal implant device industry has experienced significant growth in recent years. Examples of such growth include the development of disc replacement devices which may be implanted into a patient's spine. Tissue implants are also being developed. The goal of such disc arthroplasty and other implants is to restore normal joint height, stability and physiological movement within the patient.

As with other medical devices, disc arthroplasty and other implant devices must undergo in vitro testing before they can be placed within a patient. Such testing is often required before clinical trials by the Food and Drug Administration (FDA). Ideally, testing would be in a manner that is reflective of the combined motion and loading patterns within the human musculoskeletal structure. However, state-of-the-art testing devices are limited in their ability to reproduce a full range of human movements. Further, state-of-the-art testing devices may not accurately apply loads in a multi-axial environment. In this respect, the relative movement between adjacent spinal vertebrae defines a complex, highly mobile articulating system that is difficult to reproduce.

The spinal articulating system provides for three-dimensional motion between each vertebra. FIG. 1 illustrates individual vertebra movements with reference to the anatomical planes. Six degrees of freedom are demonstrated representing vertebral motion.

In FIG. 1, a single motion segment unit of two vertebrae 10 and interconnecting disc 15 is shown. The vertebra 10 has an anterior side 14 and a posterior side 12. Three anatomical axes defined as "x," "y," and "z" are provided. The three axes "x," "y," and "z" converge at the vertebra 10. The "y" axis represents an axis about which flexion and extension occur; the "z" axis represents a vertical axis about which axial rotation occurs; and the "x" axis represents an axis about which lateral (or side) bending occurs.

The "x," "y," and "z" axes also form three anatomical planes (not indicated). The plane defined by the "z-y" axes is the frontal plane; the plane defined by the "x-z" axes is the sagittal plane; and the plane defined by the "x-y" axes is the transverse plane. Flexion and extension occur within the sagittal plane, while lateral bending occurs within the frontal plane.

It is also understood that the vertebra 10 is capable of translation along the "x," "y," and "z" axes. Thus, the six degrees of freedom, or DOF, represented in FIG. 1 are (1) translation (or displacement) along the "x" axis; (2) rotation about the "x" axis; (3) translation along the "y" axis; (4) rotation about the "y" axis; (5) translation along the "z" axis; and (6) rotation about the "z" axis.

In actual physiological conditions, the vertebra 10 will undergo forces and moments about the "x," "y," and "z" axes. FIG. 2 presents a human head 20 exhibiting lateral bending motion. This means that the head 20 is rotating within the frontal plane of FIG. 1. To accommodate bending, a cervical spine 25 is shown. In the left view 22, the head 20 and spine 25 are being bent to the left; in the center view 24, the head 20 and spine 25 are in a neutral position; and in the right view 26, the head 20 and spine 25 are being bent to the right. It is noted in the left-bending 22 and right-bending 24 views, the head 20 and spine 25 are also being rotated axially about axes that lie within the frontal plane and move with the spine as it laterally bends. This is because maximal axial rotations cannot occur without lateral bending, and visa-versa. Arrows indicate these combined movements. Similarly, the range of flexion-extension motion permissible is dependent on the degree of left-right axial rotation.

It is desirable to have laboratory testing systems that are capable of replicating the multi-axial motions (such as motions 22 and 26 shown in FIG. 2) and loads experienced in vivo. However, because of the kinematic complexities involved in defining and testing spinal movement, researchers have often simplified analysis of spinal movements to a two-dimensional case. In a two-dimensional (2-D) study, motion is constrained to only one of the anatomic planes, typically the sagittal plane. The sagittal plane exhibits the least out-of-plane motion and is the most common choice for 2-D analysis.

Another shortcoming to most testing machines in commercial use today is that they apply a pure bending moment to a spinal test specimen. The relative vertebral rotations induced at the various spinal levels due to applied pure moments do not agree with those observed in vivo. For example, systems that load the sub-axial cervical spine using a pure moment load induce the greatest flexion-extension motion towards the outer spinal bodies, that is, C3-C4 and C6-C7. This is in direct contrast to a multitude of in vivo data in which the greatest motions have been reported to occur in the mid-spine region, typically at C4-C5 and C5-C6. Thus, commonly employed pure moment protocols do not replicate sagittal plane in vivo spinal kinematics. In addition, and as noted above, such a two-dimensional testing system only replicates a small portion of actual human movements.

Previous efforts towards robotics-based testing of the spine have been limited to either pure displacement control methods, or slow, quasi-static force control approaches. Pure displacement control methods involve application of predetermined motions to a test specimen and the measurement of resulting forces. Quasi-static force control approaches involve an iterative method whereby a small incremental displacement is applied to a spinal body and the forces measured. The position of the spinal body being moved is then readjusted by small amounts in specific directions according to a governing algorithm until predetermined spinal body loading criteria are met or optimized. A subsequent small incremental displacement is applied and the process is repeated. The adjusted location points which meet the force loading criteria thus form a motion path or range of motion that can be stitched together and replayed by the robot in one large continuous motion over which spinal loading is intended to remain within some specified parameters and tolerance. Load control methods that allow a spinal test specimen to move inherently 'where it wants to' as opposed to some prescribed path are preferred. Because most scientific investigations of spinal joints and/or added instrumentation involve comparison of different spinal conditions subjected to an identical loading input, pure displacement control methods have limited investigational use. Quasi static load control approaches are cumbersome and extremely time consuming to complete one full spinal body motion over a full physiologic range. Further, because of the stop start nature of quasi-static tests, the full dynamic nature and response of the tissue under investigation may not be realized.

None of the conventional laboratory testing systems is capable of replicating or evaluating the combined motion and loading patterns associated with the human spine. In vivo physiologic spinal movements cannot be fully tested or described by motions along a single axis or within a single plane. In this respect, in vivo physiologic spinal movements involve motion in more than one plane. Further, conventional laboratory test systems are typically programmed around independent control of each available degree of freedom. Conventional laboratory systems as such do not possess a sufficient number of, and appropriate composition of, controllable degrees of freedom that can be simultaneously coordinated to input motion and force parameters that can induce a full range of physiologic and coupled spinal movements.

Therefore, a need exists for an in vitro spinal testing system that enables the simulation of in vivo vertebral body motion in space, and that can maintain target end loads in real time. Further, a need exists for a multi-axis, programmable, in vitro testing system for tissue and implant testing that is capable of investigating coupled joint movements. Still further, a need exists for a programmable, in vitro testing system that applies specified end loads to a spinal specimen throughout a physiologic range of motion.

SUMMARY OF THE INVENTION

A multi-axis, programmable testing system is provided. The testing system is used for testing coupled joints such as vertebral joints. The coupled joint is mounted within the system so as to provide a fixed end and a moving end. In one aspect, the system includes an actuation system operatively connected to the moving end of the coupled joint for imparting at least four degrees of freedom. The actuation system may be a servo system, a stepper motor system, a hydraulic system, a pneumatic system, or a magnetic system.

A first force sensor is disposed between the actuation system and the moving end of the coupled joint for sensing applied force. A second force sensor may optionally be disposed at the fixed end of the coupled joint for sensing transmitted force.

A controller is also provided in the testing system. The controller applies selected forces, motions, or combinations thereof to the moving end of the coupled joint. In one aspect, the controller receives input signals in order to apply the selected forces, motions, or combinations thereof within the four degrees of freedom.

In one embodiment, a servo actuation system is used having a first rotary actuator for imparting rotation to the coupled joint about an axis orthogonal to the plane of motion, and a second rotary actuator for imparting rotation to the coupled joint about an axis orthogonal to the first rotational axis and moving within the plane of motion. Preferably, the first and second rotary actuators operatively interact through a gimbal connection. In one aspect, the first and second rotary actuators are each capable of providing rotation of at least 180°.

The servo actuation system may further include a first linear actuator for imparting translation to the coupled joint along a first translational axis, and a second linear actuator for imparting translation to the coupled joint along a second translational axis, the first and second translational axes forming a plane of motion. In one aspect, the first and second linear actuators provide travel of about 200 mm to about 700 mm.

As noted, the coupled joint may be a spinal specimen. The spinal specimen may include at least one spinal motion segment unit. In one aspect, the spinal specimen is at least a portion of a cervical spine, a thoracic spine, a lumbar spine, or combinations thereof. The motion segment unit may be either a model or a cadaveric sample. In one implementation, the spinal specimen may include a spinal implant.

Various types of sensors may be used for the testing system. In one aspect, the first and second force sensors each define a six-axis sensor. In another aspect, the actuation system itself imparts not just four, but six degrees of freedom to the moving end of the coupled joint.

The four degrees of freedom may comprise a first translational degree of freedom along a first translational axis, a second translational degree of freedom along a second translational axis, the first and second translational axes forming a first plane of motion, a first rotational degree of freedom about a first rotational axis orthogonal to the first plane of motion, and a second rotational degree of freedom about a second rotational axis orthogonal to the first rotational axis and moving within the first plane of motion.

It is preferred that the testing system also include a frame. The frame defines a volume for receiving and supporting the coupled joint. Preferably, the testing system volume is capable of receiving coupled joints of varying lengths. For instance, the testing system may receive and test a model of a substantial portion of a human spine. In one aspect, the coupled joint is supported within the frame in a vertical orientation. In this instance, the system may further include a lower clamping fixture for releasably supporting the fixed end of the coupled joint, and an upper clamping fixture for releasably supporting the moving end of the coupled joint.

In one aspect, the first translational degree of freedom originates along a first horizontal axis, and the second translational degree of freedom originates along a second vertical axis. The first horizontal axis and the second vertical axis form the first plane of motion. The first rotational degree of freedom about the first rotational axis is orthogonal to the first plane of motion and the second rotational degree of freedom about the second rotational axis is orthogonal to the first rotational axis and moves within the first plane of motion.

In one embodiment, the actuation system imparts six degrees of freedom to the moving end of the coupled joint. The six degrees of freedom comprise:

the first translational degree of freedom originating along a first horizontal axis, and the second translational degree of freedom originating along a second vertical axis, the first horizontal axis and the second vertical axis forming the first plane of motion;

a third translational degree of freedom originating along a third horizontal axis orthogonal to the first horizontal axis, the second vertical and third horizontal translational axes forming the second plane of motion;

the first rotational degree of freedom about the first rotational axis that is within the first plane of motion and parallel to the first horizontal axis.

the second rotational degree of freedom about the second rotational axis that is orthogonal to the first rotational axis and moves within the second plane of motion; and a third rotational degree of freedom about the third rotational axis that is orthogonal to the second rotational axis and moves within a plane orthogonal to the second rotational axis.

An alternate embodiment of a testing system is provided herein. The testing system is again used for testing coupled joints such as vertebral joints. The coupled joint is mounted within the system so as to provide a fixed end and a moving end. In one aspect, the system includes an actuation system operatively connected to the moving end of the coupled joint for imparting at least four degrees of freedom. A first force sensor is disposed between the actuation system and the moving end of the coupled joint for sensing applied force. A second force sensor may optionally be disposed at the fixed end of the coupled joint for sensing transmitted force.

A controller is also provided in the alternate testing system. The controller selectively directs input signals to the control actuation system in order to simultaneously apply selected forces and motions to the moving end of the coupled joint such that a loading pattern is provided that correlates to a human physiologic response.

BRIEF DESCRIPTION OF THE DRAWINGS

So that the above recited features of the present invention can be better understood, certain drawings, flow charts and/or photographs are appended hereto. It is to be noted, however, that the appended figures illustrate only selected embodiments of the inventions and are therefore not to be considered limiting of scope, for the inventions may admit to other equally effective embodiments, formats and applications.

FIG. 4A demonstrates a block being moved horizontally in a plane defined by the "x" and "y" axes. This is translational movement.

FIG. 4B demonstrates the block being rotated within a plane defined by the "x" and "z" axes. This is rotational movement about the "y" axis.

FIG. 4C demonstrates the block being rotated within the plane defined by the "x" and "y" axes. This is rotation about the "z" axis.

DETAILED DESCRIPTION

Definitions

The term "coupled joint" refers to joints within the human body that enjoy relative motion. Nonlimiting examples of a coupled joint include various spinal vertebrae such as the cervical, thoracic and lumbar vertebrae.

The term "spinal implant" refers to any natural or artificial device or instrumentation of any composition that may be either permanently or temporarily installed into the human spine. A non-limiting example is a disc replacement device. Instrumentation may include fusion devices, restoration devices, and motion preservation devices.

"Controller" means any system that provides input in order to control motion and force parameters. Non-limiting examples include vision-guided and encoder position-guided systems.

The term "force" means load, and includes both torque and force.

The term "actuation system" means any system designed to provide mechanical input such as motion or force.

The term "control system" means any system designed to control at least one of direction, speed, force and distance.

The term "spinal motion segment unit" means two adjacent vertebral bodies with an intermediate disc.

The term "spinal specimen" refers to any portion of the cervical, thoracic or lumbar spine. The spinal specimen may have a skull connected to a proximal end of the cervical spine, or a sacrum attached to a distal end of the lumbar spine. The spinal specimen may be a cadaveric sample, or an artificial model. The spinal specimen may be a cadaveric sample having a discectomy, ligament resection, laminectomy, facetectomy or a corpectomy. The spinal specimen may or may not have a spinal implant.

Description of Specific Embodiments

Figure 3:
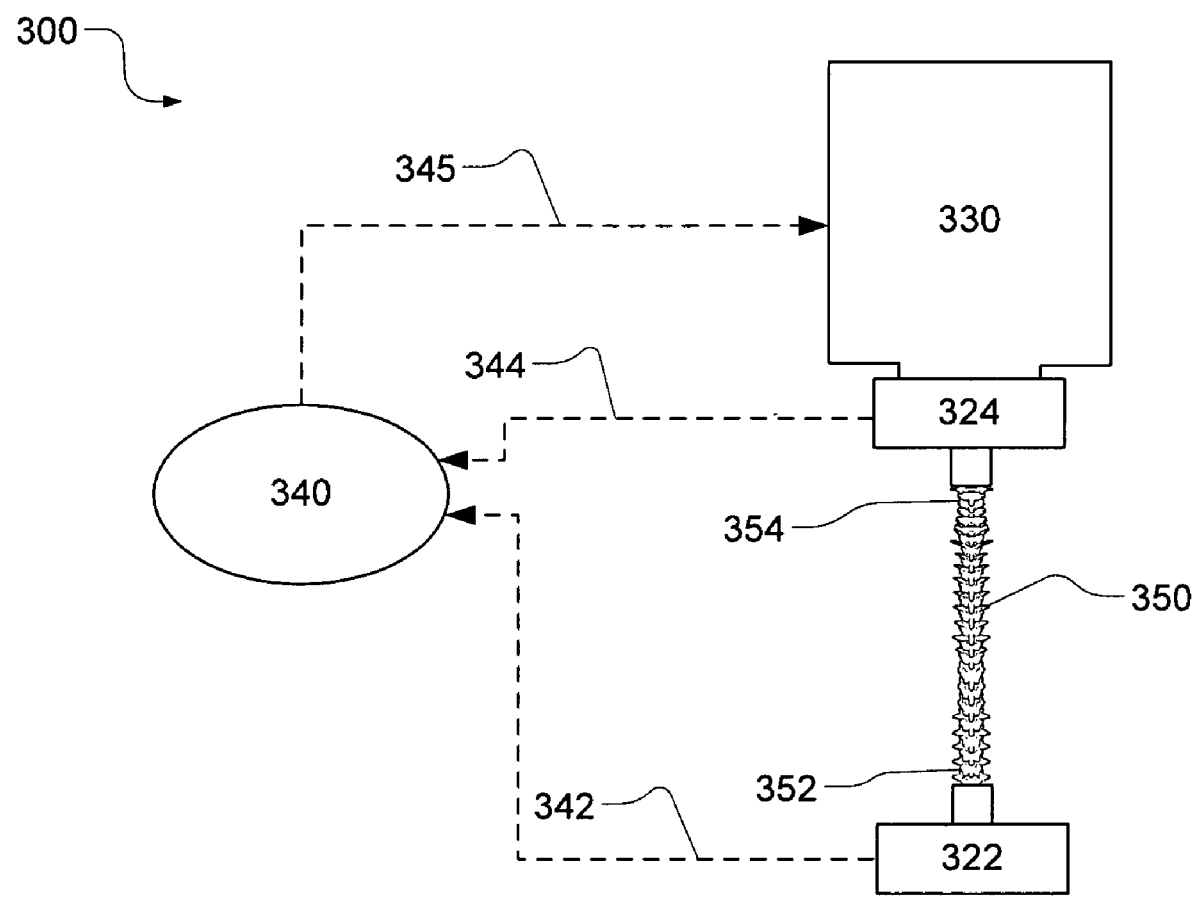
FIG. 3 presents a schematic representation of the coupled joint testing system of the present invention, in one embodiment. A test specimen is shown within a volume defined by a frame of the testing system.

FIG. 3 presents a programmable, multi-axis testing system 300 of the present invention, in one embodiment. In FIG. 3, the testing system 300 is shown schematically. The testing system 300 is designed to test a specimen 350 by subjecting the specimen 350 to predetermined motion and force parameters. The system 300 offers a hybrid control scheme that enables the simulation of in vivo body motions in space while simultaneously maintaining target end loads in real time.

The test specimen 350 within the testing system 300 is a coupled joint. The test specimen 350 may be of any type of coupled joint within the human body. Non-limiting examples include the wrist, the shoulder, the hip, and the spine. Preferably, the test specimen 350 is a portion of a human spine.

The human spine defines a series of coupled joints. The coupled joints are designed to provide flexibility and structural support for the body, neck and head. In addition, the vertebral joints that make up the spinal column serve as a protective conduit for the major nerves leading to and from the brain. For purposes of the testing system 300, the test specimen 350 may be the entire length of the spine from the torso to the head, or may be a portion of the spine such as some or all of the vertebrae within the lumbar, thoracic or cervical spine. In FIG. 3, the test specimen 350 is intended to represent the vertebrae.

The spinal test specimen 350 may be a model. Alternatively, the spinal test specimen 350 may be a cervical portion from a cadaver. The specimen 350 may be of any length. In this respect, the testing system 300 is designed to be adjustable so as to fit any series of coupled vertebrae, even from the torso to the head. In one aspect, a portion of a spinal column representing only two or up to ten adjacent vertebrae is tested.

The most proximal section of the spine is referred to as the cervical spine. The cervical spine is comprised of cervical vertebrae one through seven (C1 to C7). Vertebra C1 is an atypical vertebra, and is generally omitted from testing as a cervical joint. The majority of the discussion herein relates to the testing of the sub-axial cervical vertebrae, primarily C2 through C7. In one aspect, the spinal specimen 350 is any grouping of C2-C7 vertebrae. However, it is understood that the present system may be used to test any coupled joint and implants therein.

The movements within a test specimen 350 such as a cervical spine may be defined in terms of degrees of freedom. FIGS. 4A through 4C demonstrate four degrees of freedom. Each figure shows movement of a block 400 within a right orthogonal Cartesian coordinate system.

FIG. 4A demonstrates a block 400 being moved horizontally along an "x" axis, and then vertically up a "z" axes. The horizontal and vertical movements represent two translational movements. In this illustration, horizontal movement is shown by line 410 while vertical movement is represented by line 415. These represent a first degree of freedom and a second degree of freedom, respectively. Upon movement, new axes "x'", "y'", and "z'" are shown defining a new position for block 400.

FIG. 4B demonstrates the block 400 being rotated within a plane defined by the "x" and "z" axes. More specifically, rotation is within the "x'"-"z'" plane. This is rotational movement about the "y'" axis. This is a third degree of freedom and represents an in-plane rotation about an axis orthogonal to the horizontal and vertical axes. The rotation is demonstrated at arrow 420. The resulting movement produces a new position defined according to axes "x''," "y''," and "z''." The rotation 420 may be clockwise or counter-clockwise.

FIG. 4C demonstrates the block 400 being rotated again, but now within the plane defined by the "x" and "y" axes. More specifically, rotation is within the "x''''-"y''''" plane. This is a fourth degree of freedom and represents an out-of-plane rotation about the newly located vertical or "z''''" axis. The rotation is demonstrated at arrow 430. The rotation 430 may be clockwise or counter-clockwise.

Figure 1:
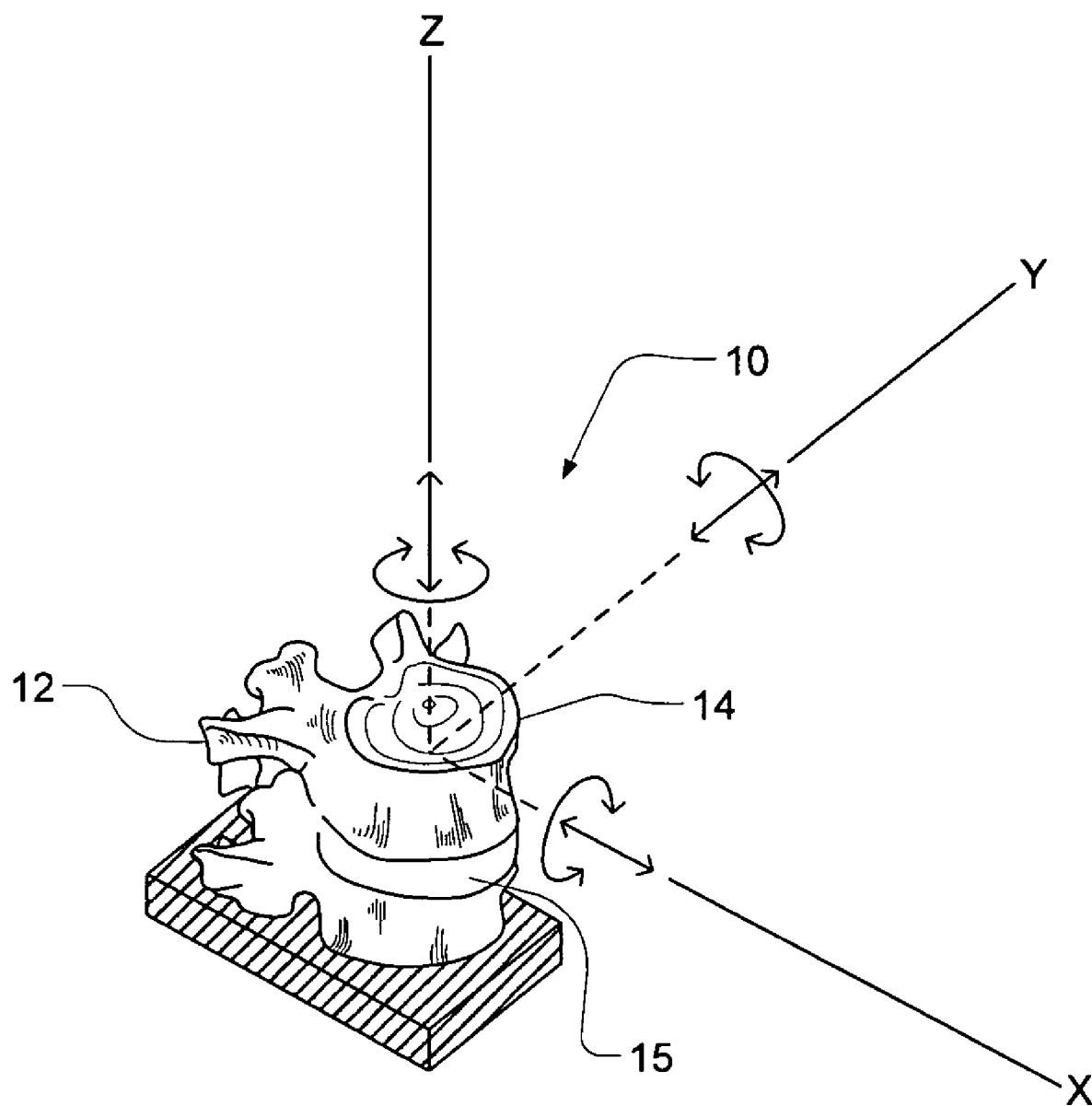
FIG. 1 illustrates individual vertebra movements with reference to the anatomical planes. Three anatomical axes defined as "x," "y," and "z" are provided.
Figure 2:
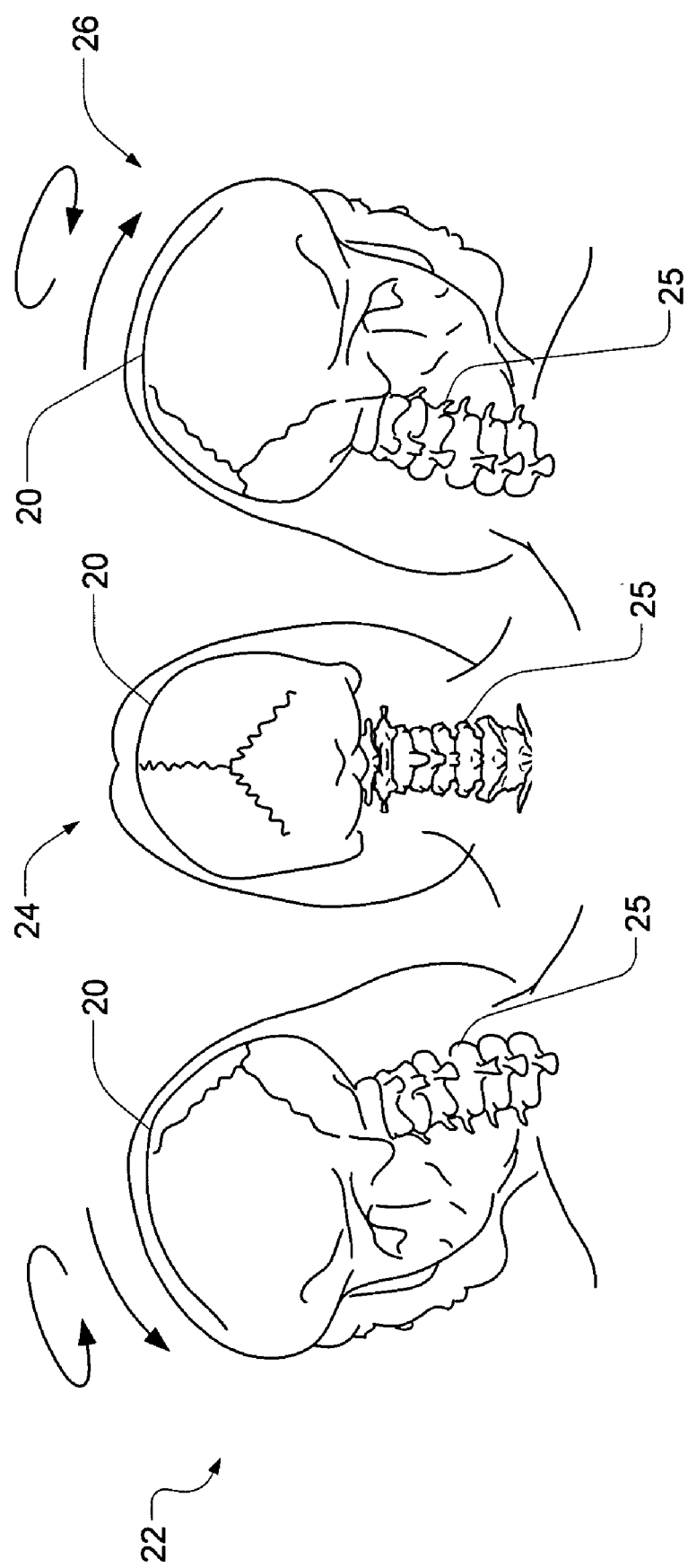
FIG. 2 illustrates coupled lateral bending and axial rotation motions in the cervical spine. In the left view, a head is being bent to the left; in the center view, the head is in a neutral upright position; and in the right view, the head is being bent to the right.
Figure 4:
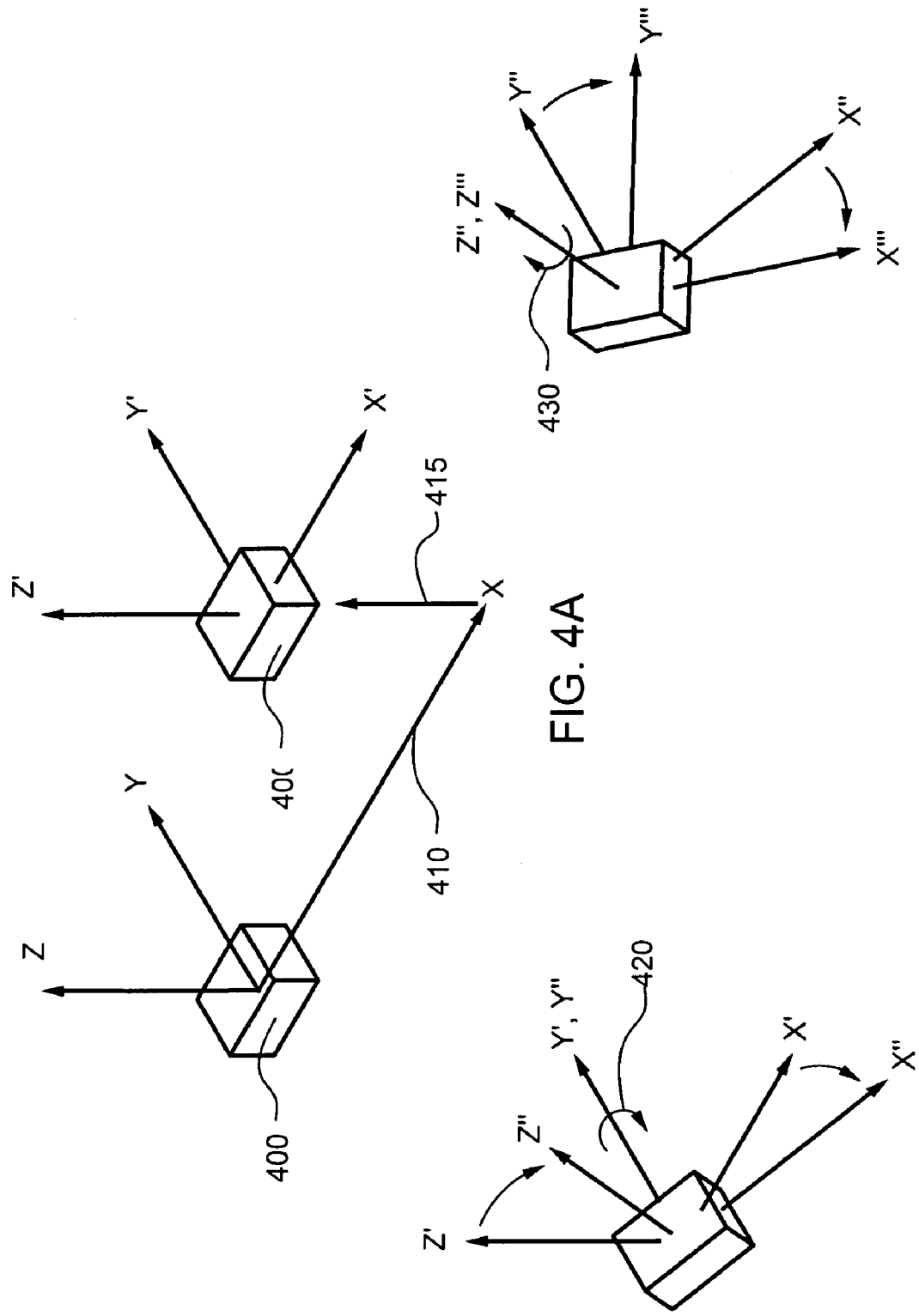
FIGS. 4A through 4C demonstrate four degrees of freedom. Each figure shows a three dimensional coordinate system.

The following correlations between FIG. 4 and FIG. 1 may be made:
horizontal translation 410 correlates to movement along the forward axis "x" in FIG. 1;
vertical translation 415 correlates to movement along the vertical axis "z" from FIG. 1;
in-plane rotation 420 corresponds to rotation within the sagittal plane about the lateral bending axis "y;" and
out-of-plane rotation 430 corresponds to axial rotation about the vertical "z" axis of FIG. 1.

Motions 410, 415, 420, and 430 define four degrees of freedom for coupled joint testing. It is noted that a test specimen 350 may be rotated 90 degrees within the testing system 300 in order to change the plane of motion to coincide with the anatomical frontal plane. The testing system 300 itself is not moved, but the test specimen 350 is. In the context of a cervical spine specimen, orthogonal rotation converts the in-plane rotation from rotation within the sagittal plane about the flexion extension axis "y," to rotation within the frontal plane about the lateral bending axis "x."

Figure 5:
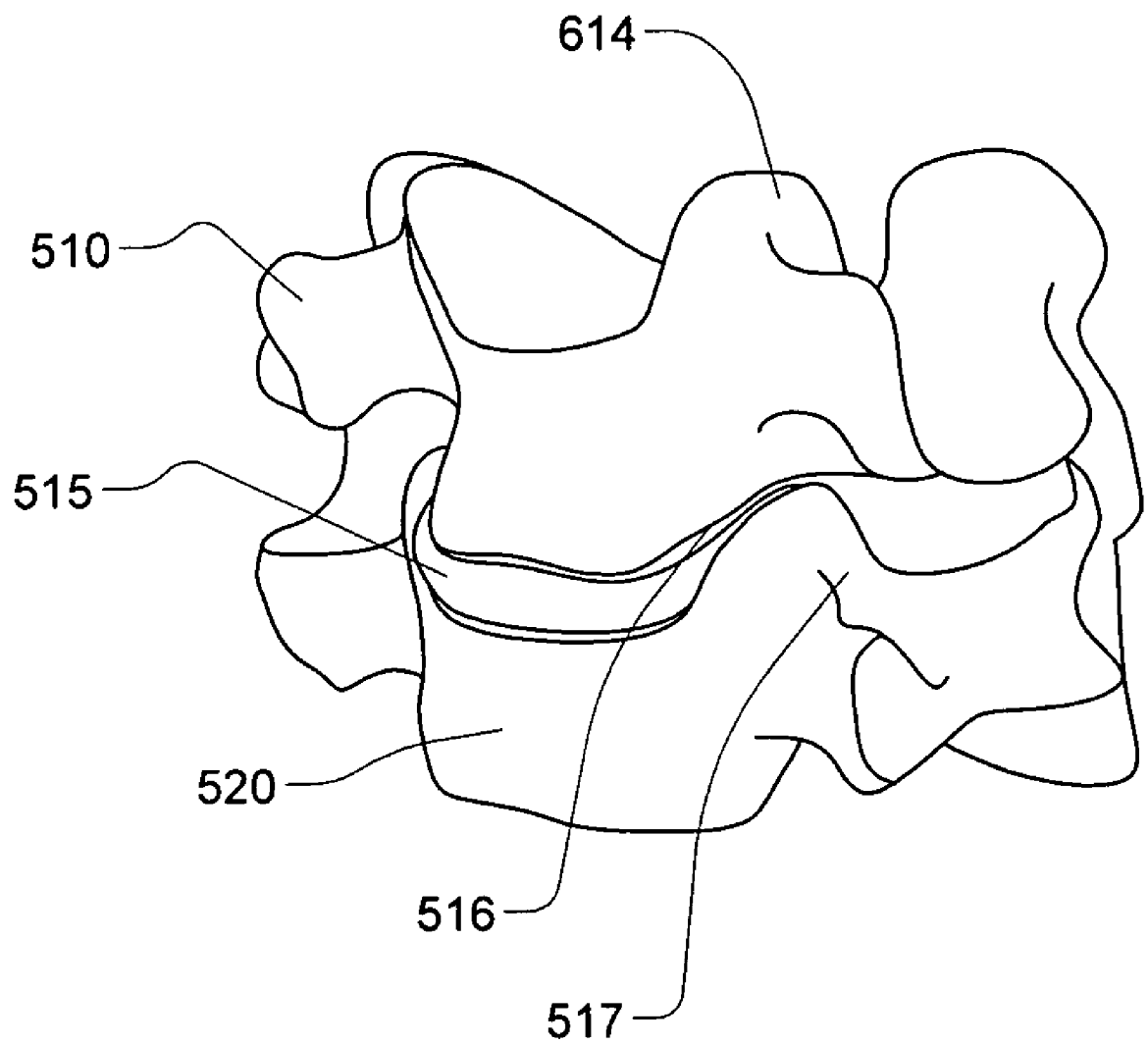
FIG. 5 is a perspective view of a portion of a spinal specimen as may be tested in the testing system. The spinal specimen portion comprises two adjacent cervical vertebrae and interconnecting disc.

FIG. 5 is a perspective view of a spinal specimen 500 as may be tested in the system 300. The spinal specimen 500 comprises two adjacent cervical vertebrae 510, 520. Spinal specimen 500 in FIG. 5 is one example of a spinal specimen that may be tested in the system 300. It is understood that when the specimen 350 in FIG. 3 is a spinal specimen, it will typically have more than two vertebrae. It is also understood that a spinal specimen is not limited to cervical vertebrae, but may be any portion of the vertebrae.

Figure 6:
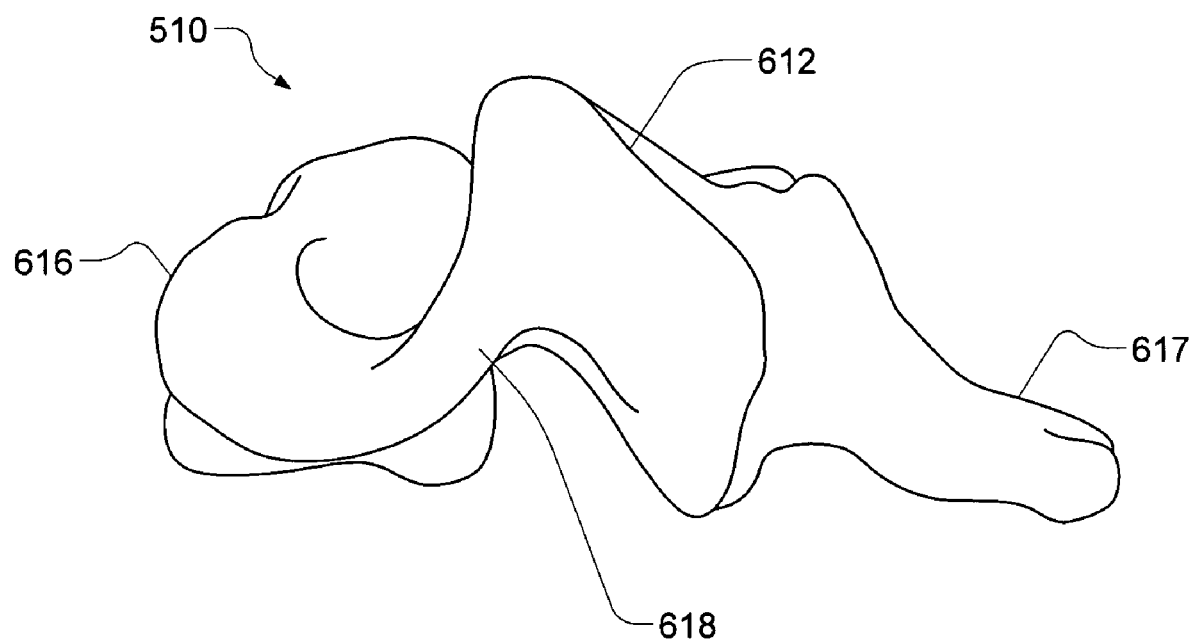
FIG. 6 is a perspective view of a single vertebra from FIG. 5.

FIG. 6 is a perspective view of a single cervical vertebra 510 from FIG. 5. The single cervical vertebra 510 is offered for further clarity and description of the vertebral structure. Cervical vertebra 510 is representative of any vertebra from C2 through C7.

Referring now to both FIG. 5 and FIG. 6, vertebra 510 first comprises a body 612. The vertebral body 612 is located in an anterior portion, and carries about two thirds of the load for the vertebra 510. The body 612 is comprised of a core of cancellous bone surrounded by a thin shell of cortical bone. The body's 612 upper surfaces are concave from side to side, but convex in an antero-posterior (AP) direction. The body 612 has a raised projection called the uncinate process 614 that forms an articulation with an inferior articular surface of the proximally adjacent vertebra 520. This mating arrangement forms what is known as the uncovertebral joints 516. These may also be referred to as joints of Luschka.

The vertebra 510 includes several additional "processes." The processes include an anterior tubercle of transverse process 616, a spinous process 617, and a posterior tubercle of transverse process 618. These processes 616, 617, 618 provide regions of muscular attachment, and also act as lever arms for relative movement between adjacent vertebrae 510, 520.

The vertebra 510 also has a lower surface (not seen). The lower surface of the vertebral body 612 is convex from side to side, and concave in the AP direction. The lower surface rests upon a disc 515. A facet 517 exists on each of the posterior lateral aspects of the vertebrae 510 and 520.

Figure 7:
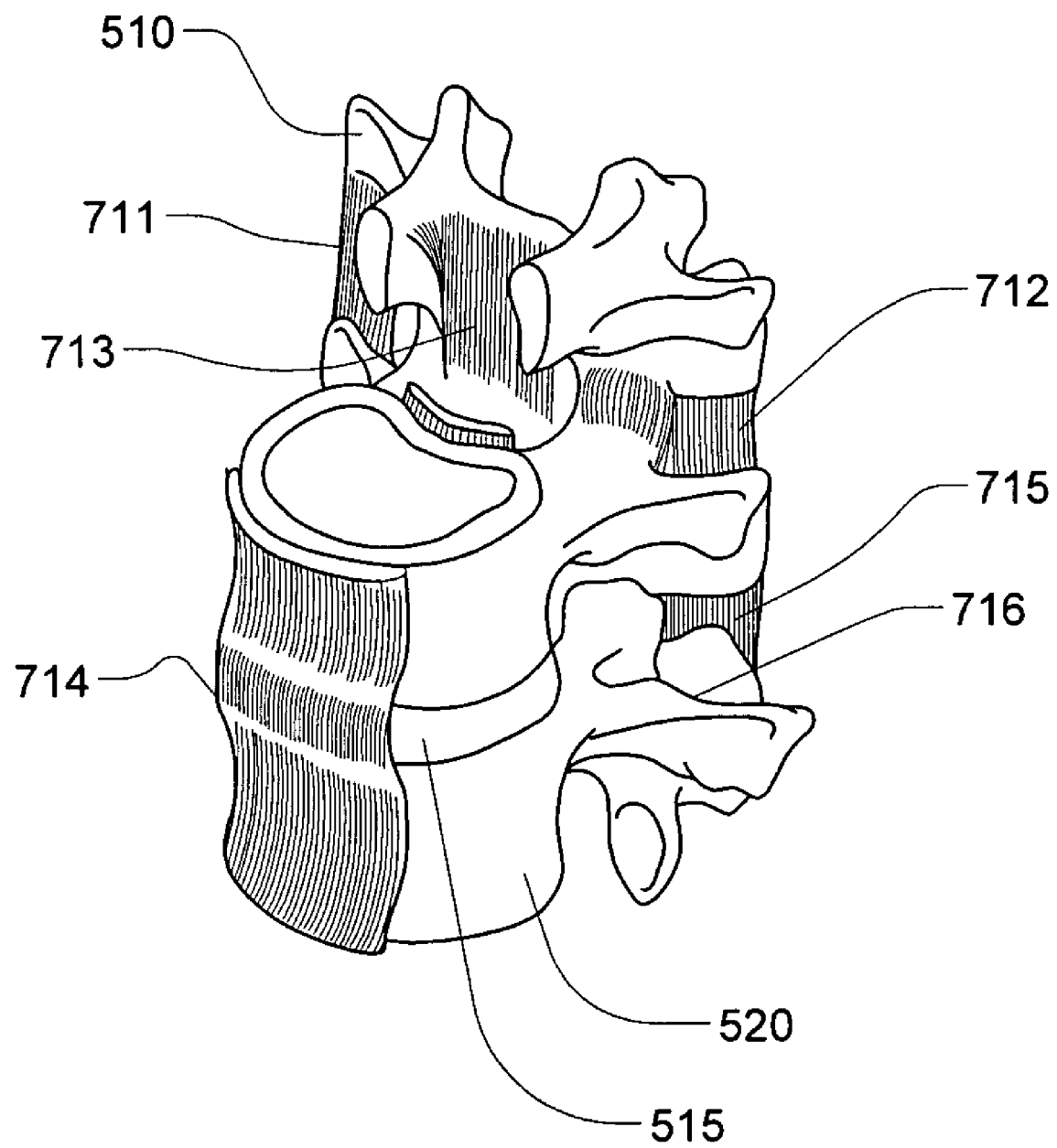
FIG. 7 is perspective view of the spinal specimen of FIG. 5, showing ligaments added.

Interconnecting the cervical vertebrae are ligaments. FIG. 7 provides a perspective view of the cervical vertebrae 510, 520, with various ligaments seen. The ligaments generally include an intertransverse ligament 711, a facet capsular ligament 712, a posterior longitudinal ligament 713, an anterior longitudinal ligament 714, an interspinous ligament 715, a supraspinous ligament 716 and a ligament flavum 717.

The ligaments 711, 712, 713, 714, 715, 716, 717 are comprised of various proportions of collagen fibers (for strength), elastin fibers (for flexibility) and rectin fibers (for mass). The ligaments 711, 712, 713, 714, 715, 716, 717 are uni-axial structures and can only resist load in tension. Thus, a ligament's stabilizing effect between two vertebral bodies (such as 510 and 520) depends on the type of motion and the distance from the ligament to the center of rotation of the motion. For example, the anterior longitudinal ligament 714 compresses during flexion, and thus provides no resistance. In contrast, the more posterior ligaments, such as the ligament flavum 717 and the interspinous ligament 715 come under the greatest tension during flexion, thereby providing resistance and stability to the spine. Tensile failure loads for ligaments of the cervical spine range from 35 N to 200 N.

An intervertebral disc 515 is located between individual vertebrae 510, 520. In the spinal specimen 500 of FIGS. 5 and 7, the intervertebral disc 515 is a cervical disc. The cervical disc 515 is attached to the end plates (not seen) of each vertebral body 612. The disc 515 is slightly thicker anteriorly contributing to an overall lordotic curvature of the cervical spine. Structural components of the disc 515 include collagen, proteoglycans, and water, which together comprise 95 percent of the disc volume.

The disc 515 can be divided into two major regions: a normally gelatinous central region called the nucleus pulposus, and an outer series of supporting rings called the annulus fibrosis. A full disc with these components is not shown, but those of ordinary skill in the art of spinal implants will be well familiar with the makeup of the disc structure. Under normal healthy conditions, the nucleus pulposus serves to evenly distribute external forces applied to the disc over the annulus fibrosis and vertebral end plates. Maintenance of this function depends upon a normally high concentration of proteoglycans, which are strongly hydrophilic and therefore maintain water content of the disc 515.

It is thought by some that changes in the proteoglycan content of the nucleus pulposus can, with time and age, inhibit the capacity of the disc 515 to hold water. Secondary to this loss of water content, degenerative changes can also begin to appear in the annulus fibrosis. This degeneration represents a cellular response to changes in load patterns on the disc 515. Over time, this weakening may lead to herniation of the nucleus pulposus. Protrusion of the nucleus pulposus and subsequent contact against nervous tissues of the spine can lead to sensory and motor changes.

Degeneration of a disc 515 and subsequent loss of its normal mechanical function is one initiating step in the development and onset of spinal disc disease. The causes of disc disease appear to be multi-factorial, and may include biomechanical stresses, biochemical abnormalities, genetic susceptibility and autoimmune processes. Presumably, one or more of these initiating factors leads to a breakdown of the biochemical integrity of the disc 515. As changes begin to take place in a disc 515, the spine becomes subject to a series of degenerative conditions. The sequence of such conditions in order of increasing severity is cervical spondylosis, cervical radiculopathy, and cervical myelopathy. This progression generally results from age-related degenerative changes described above, but can also arise from trauma. The least severe condition, to wit, cervical spondylosis, can be asymptomatic, but may also produce neck pain due to distortion of innervated areas of the joint disc. Cervical radiculopathy and myelopathy involve more severe impingement of spinal nerves.

More advanced cases of cervical radiculopathy and myelopathy as well as incidences of trauma often require surgical intervention. Various surgical procedures are available for decompression of neural elements and include removal of the disc 515 with or without fusion of the vertebral bodies 510, 520 involved. Other surgical options include anterior cervical corpectomy and strut graft fusion, and posterior cervical laminectomy.

A relatively new surgical approach for the treatment of cervical spinal disc diseases is that of artificial cervical disc replacement. The goals of this surgery are to restore and maintain disc height, reduce pain, and maintain joint stability with normal joint motion. In general, there are two basic types of intervertebral disc prostheses: devices that replace the nucleus pulposus only, and devices that replace the entire disc. A variety of devices are currently in use in Europe, and are now undergoing clinical trials in the United States.

In the context of the cervical spine, it is desirable to develop a simulator which replicates the flexion-extension motions of the neck in combination with left-right axial rotations. This allows for the testing of implants to the cervical spine. For instance, as the cervical spine flexes or extends and axially rotates, individual vertebrae rotate and translate within the sagittal plane. To replicate this motion, control over multiple planar movements representing at least four degrees of motion is desired. In addition, it is desirable to apply motion and load inputs to a free end of the spine while the opposing end remains fixed. This approach has the advantage of applying target end loads that can be mathematically defined and controlled.

Referring again to the spinal test specimen 350 in FIG. 3, the specimen 350 advantageously has a fixed end 352 and a moving end 354. Preferably, the specimen 350 is oriented vertically, with the fixed end 352 at the base of the specimen 350. Reciprocally, the moving end 354 is preferably at the top of the specimen 350. However, it is understood that the spinal simulator may operate and function with the fixed end 352 at the top of the spinal specimen 350, and the moving end 354 at the bottom. Alternatively, the specimen 350 may be horizontal, with one end fixed and the other end moved. Alternatively still, the specimen 350 may be oriented at an angle between vertical and horizontal.

In order to create motion at the free end 354 of the specimen 350, an actuation system 330 is provided. The actuation system 330 induces movement in the four degrees of freedom as discussed in connection with FIG. 4. Any of the four controlled degrees of freedom and/or the other two axes may be made to be passive, or decontrolled, or not employed at all. In the embodiment shown in FIG. 3, servo actuation system 330 is positioned above the spinal test specimen 350. The actuation system 330 is operatively engaged with the moving end 354 of the specimen 350 so as to transmit motion, forces, or combinations thereof to the moving end 354. In the preferred embodiment, the actuation system 330 is a servo system that comprises a plurality of motors and gimbals which apply motions, forces and torque in selected directions. The hardware for applying forces and loads is discussed below in connection with FIGS. 8 and 9.

It is noted that all forces and torque are applied to the moving end 354. Rigorous kinematic analysis would be required to determine the relative positioning between two moving spinal end bodies at any given instance. Therefore, the approach selected for the system 300 is to apply all motion and load inputs to one free end 354 of the test specimen 350 while the opposing end 352 remains fixed.

The amount of force transmitted by the actuation system 330 is controlled. To this end, force sensors 322, 324 are provided. The force sensors 322, 324 are preferably six-axis sensors, capable of measuring force in each direction of motion. Force sensor 322 is positioned below the fixed end 352 of the spinal specimen 350. Reciprocally, force sensor 324 is disposed between the servo actuation system 330 and the moving end 354 of the spinal specimen 350. The two, six-axis force sensors 322, 324 measure and provide force feedback of specimen 350 loading. Force sensor 324 located at the moving end 354 measures applied loads, while force sensor 322 located at the fixed end 352 measures transmitted load.

In order to control the actuators in the actuation system 330, an industrial robotic motion controller 340 may be provided. The controller 340 is used to command and coordinate all motion and load inputs to the spinal specimen 350. The controller 340 receives force and torque information from the force sensors 322, 324, and solves the kinematic transformation matrices necessary to plan trajectory paths for the multi-axis movements. In one aspect, the controller 340 is integrated with the actuation system 330 and the force sensors 322, 324 in order to form a closed loop, multi-axis position servo control system that has fixed end 352 stability.

In order to provide motion and load instructions to the actuation system 330, input signals are provided. A signal line is shown at 345. It is understood that signal line 345 is schematic, and may represent either a wired or a wireless communication means. In the case of a wired line 345, the line may be electrical, fiber optic, or other arrangement. Further, it is understood that signal line 345 may branch to various motors, typically through a bus or wiring panels (not shown). Still further, the line 345 may accommodate return signals from the servo actuation system 330. In this respect, certain servo motors (discussed below) include a high resolution encoder to provide precise position feedback to the controller 340.

Signal line 345 for the testing system sends signals from a hybrid control algorithm (discussed in greater detail below in connection with FIG. 10) residing on the controller 340. This gives the user flexibility to achieve desired positions as well as target loading conditions through the servo actuation system 330. Uniquely, the controller 340 of FIG. 3 is programmed to direct input signals through signal line 345 to the actuation system 330 in order to simultaneously apply selected forces and motions to the moving end 354 of the test specimen 350, and also to selectively rotate the moving end 354 of the test specimen 350 about a moving center of rotation within a selected plane.

FIG. 3 also shows that the testing system 300 includes signal lines from the force sensors 322 and 324 to the controller 340. The signal lines provide feedback to the controller 340 as to the amount of force sensed from loads applied through the servo actuation system 330.

Figure 8:
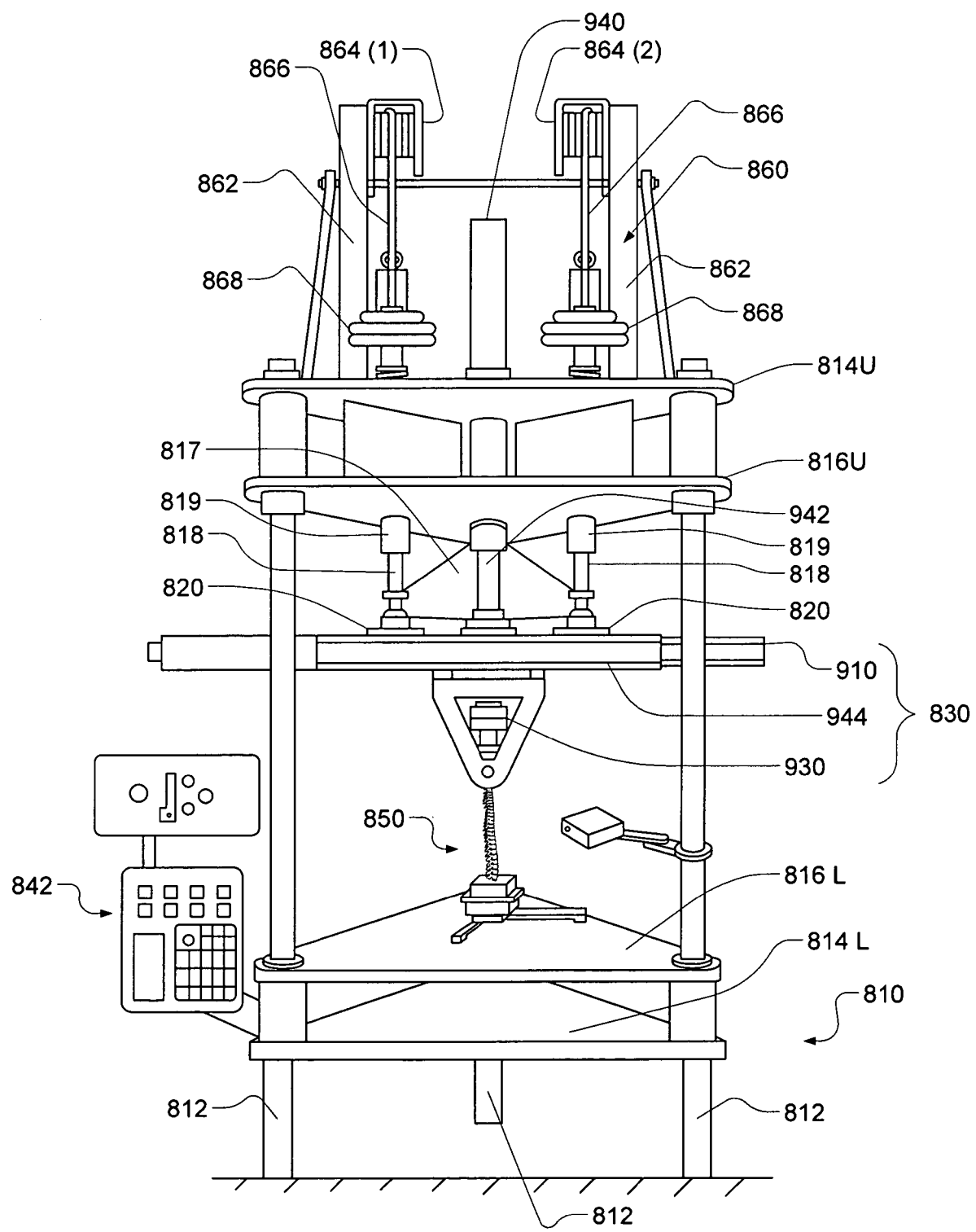
FIG. 8 is a frontal perspective view of a coupled joint testing system, in one embodiment. The representative coupled joint is a spine specimen.

FIG. 8 is a frontal perspective view of a programmable, coupled joint testing system 800, in one embodiment. The coupled joint testing system 800 is designed to test a coupled joint specimen 850 and, more particularly, a medical implant (not shown) within the test specimen. The representative coupled joint specimen 850 shown in FIG. 8 is a spine specimen.

The testing system 800 is mounted onto a tri-clamping fixture frame 810. Legs 812 support the frame 810. Stabilizing plates 814L and 814U receive and are supported by the legs 812. In addition, intermediate upper 816U and lower 816L support plates support operational hardware for the system 800. Further, a triangular plate 817 is interconnected between shaft 942 and rods 818 to provide structural support and minimize vibration.

Figure 9:
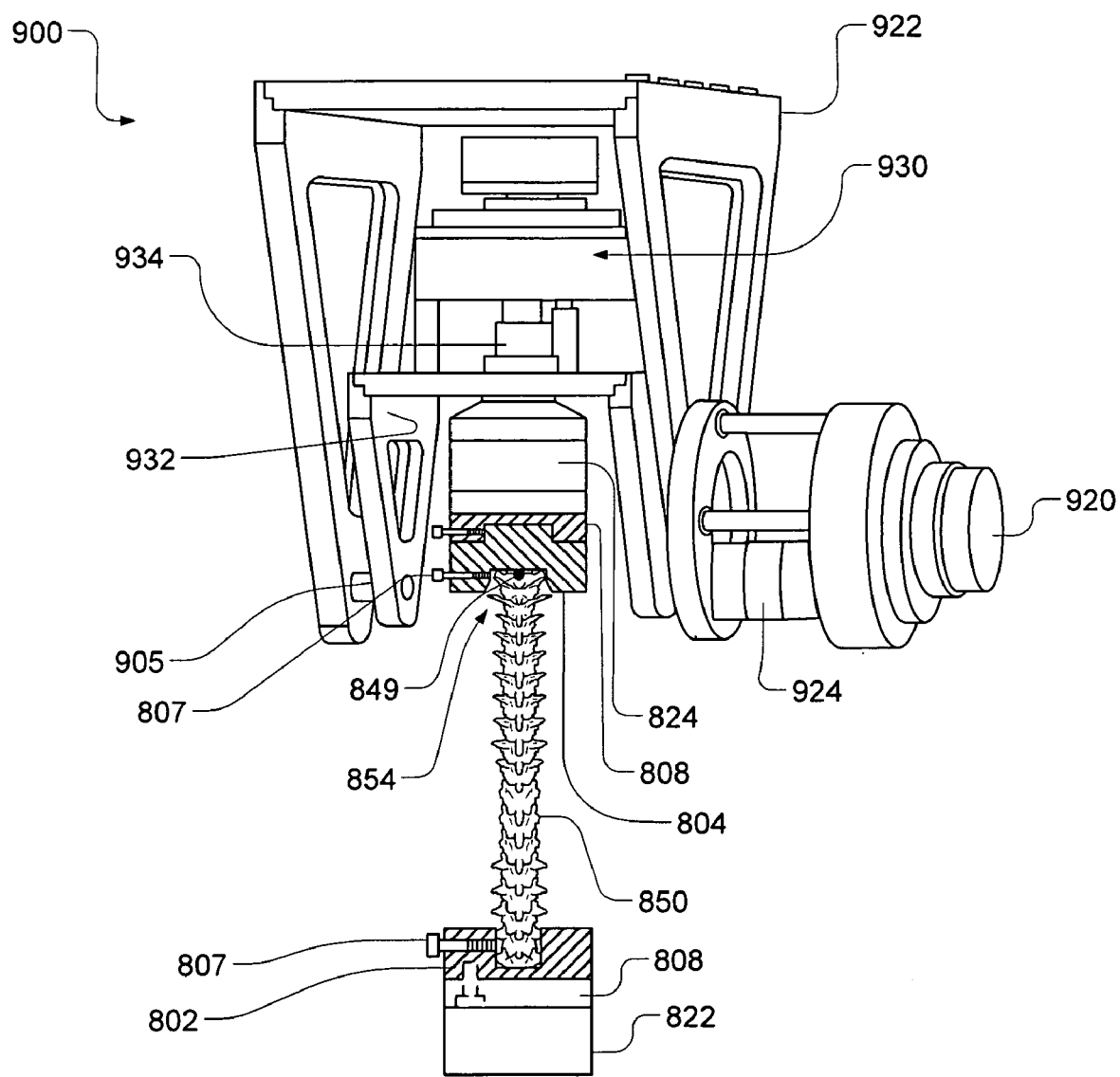
FIG. 9 is an enlarged perspective view of the actuator assembly of the coupled joint testing system of FIG. 8, in one embodiment.

A servo actuation system 830 is seen within the frame 810. In the illustrated embodiment, the actuation system 830 comprises four servo motors. Motion inputs for each of the required degrees of freedom are provided by the servo motors. The servo motors are discussed more fully in connection with FIG. 9. Three of the motors, to wit, motors 910, 930 and 940 are seen in FIG. 9. Motor 910 defines a linear motor for providing horizontal translation to the upper (moving) end of the specimen 850. Motor 930 is immediately above the coupled joint specimen 850 and provides rotational movement to the coupled joint specimen 850. Motor 940 resides above the coupled joint specimen 850 and also provides rotational movement to the specimen 850.

As noted earlier, the servo actuation system 830 is controlled by a controller. (The controller is shown schematically at 840 in FIG. 10.) A control pendant is shown in the system 800 somewhat schematically at 842. In one aspect, an industrial robotic Adept controller from Adept Technologies is used. The Adept controller may be supplied with three small electrical wiring panels. Wiring panels are shown schematically in FIG. 10 at 845.

Referring now to FIG. 9, FIG. 9 is an enlarged perspective view of a portion of the servo actuation system 830 of the coupled joint testing system 800 of FIG. 8. This portion is referred to as a gimbal assembly 900. The coupled joint specimen 850 is seen below the gimbal assembly 900. Again, the illustrated specimen 850 is a spine specimen. The specimen 850 is clamped between a lower clamping fixture 802 and an upper clamping fixture 804. Clamping screws 807 are seen securing the specimen 850 in place within the clamping fixtures 802, 804. A lower end 852 of the specimen 850 is secured within the lower clamping fixture 802, while an upper end 854 of the specimen 850 is secured within the upper clamping fixture 804. The clamping fixtures 802, 804 may be referred to as "pots."

It is noted that the method of securing the opposing ends 852, 854 of the coupled joint specimen 850 within the system 800 is a matter of designer's choice. The present inventions are not specific as to the means for supporting or holding the specimen 850. What is required is that the lower end 852 be translationally and rotationally fixed, while the upper end 854 is translationally and rotationally controlled. In addition, the spacing between the lower clamping fixture 802 and the upper clamping fixture 804 is preferably adjustable to accommodate specimens of varying lengths.

Adjacent the lower 802 and upper 804 clamping fixtures are force sensors 822, 824. The force sensors 822, 824 are also referred to as load cells. A lower force sensor 822 is positioned below the lower clamping fixture 802, while an upper force sensor 824 is positioned above the upper clamping fixture 804. The lower force sensor 822 located at the fixed end 852 correlates to force sensor 352 of FIG. 3, and measures transmitted loads. The upper force sensor 824 correlates to force sensor 354 of FIG. 3, and measures applied loads. The loads are again applied at the upper end 354.

The force sensors 822, 824 are preferably commercially available, six-axis, sensors. One suitable example of a force sensor or "load cell" is a model 100M40 from JR3, Inc. of Woodland, Calif. Another example of a suitable force sensor is the 45E15S six-axis load sensor, also from JR3, Inc. These sensors are capable of measuring three orthogonal forces and moments about an x-y-z coordinate system, where the default origin of the coordinate system of each sensor rests in the center of the load cell body. The x-y-z coordinate system of sensors 822, 824 may also be programmed to lay at any user-defined point in space in relation to the center of the sensors 822, 824.

Using the coordinate system of FIG. 1, the 100M40 load cell has an 890 N load rating about the z-axis, and a 444.8 N rating about both the x- and y-axes, respectively. The 100M40 load cell also has a 45.2 Nm torsion load rating about all axes. The 100M40 load sensor has a rated accuracy to 1% of full scale.

Using the coordinate system of FIG. 1, the model 45E15S load cell has an 8896 N load rating about the z-axis, and a 4448 N rating about the both x and y-axes respectively. The model 45E15S load cell also has a 508.5 Nm torsion load rating about all axes. The 45E15S load sensor has a rated accuracy to 0.5% of full scale.

A plate 808 is disposed between the lower force sensor 822 and the lower clamping fixture 802, or "pot." Similarly, a plate 808 is disposed between the upper force sensor 824 and the upper clamping fixture 804. The mounting plates 808 provide mechanical stability for the force sensors 822, 824 relative to the specimen 850. In one aspect, the plates 808 comprise custom fabricated, aluminum plates. In one embodiment, the plate 808 above the specimen 850 is a square stainless steel mounting plate 15.9 mm in nominal thickness. The plate 808 is bolted to the underside of the force sensor 824 to specified torque. The plate 808 below the specimen 850 is capable of transmitting force to the lower force sensor 822. The resulting slight horizontal compression of the plates 808 from the screws 807 are not considered to influence load cell 822, 824 readings.

The gimbal assembly 900 of the servo actuation system 830 supports two servo actuators 920, 930. Each of these actuators 920, 930 is a rotary actuator. Actuator 920 provides rotation to the specimen 850 about a first axis, while actuator 930 provides rotation to the specimen 850 about a moving axis orthogonal to the first rotational axis. The first rotational axis may correspond to either the frontal plane or the sagittal plane, depending upon the orientation of the spinal specimen 850 within the system 800.

The rotary actuators 920, 930 preferably offer a 360° range of motion. Further, the actuators 920, 930 preferably are capable of up to a 10 Nm continuous output torque at 0 rpm (i.e. stall torque). This torque value is much greater than torsion loads typically applied to the cervical spine, but are consistent with torsion loading applied to the lumbar spine in vitro. In one embodiment, rotary actuators 920 and 930 may apply rotational speeds of up to 2.1°/s.

A servo actuator that may be chosen for the rotational axes is a model 9FG geared servomotor, paired with a model KXA 48 servo amplifier. The 9FG model motors are supplied by Kollmorgen PMI Division, Washington, D.C. High gear reduction ratios of 150:1 within the 9FG motors permit a rated peak torque output of 10.6 Nm. A unique flat pancake design of these motors make them compact and relatively light in weight (approximately 1.5 kg each) for the rated amount of torque output.

The rotary servo actuators 920, 930 are supported by triangular frames 922, 932. Frame 922 is a large triangular frame that supports actuator 920, while frame 932 is a smaller triangular frame that supports actuator 930. In the arrangement of FIG. 9, frame 922 is an outer frame, while frame 932 is an inner frame. The triangular design for the frames 922, 932 was chosen as it is considered not only structurally sound, but also minimizes visual obstruction of the coupled joint specimen 850 itself.

The inner frame 932 is comprised of two smaller sized triangular shaped plates and a cross plate with press fit bearings (not shown) and vertical rotating shaft 934. The bottom end of the shaft 934 may be flanged to accommodate rigid mounting of the upper force sensor 924. The upper end of the shaft 934 is coupled to the shaft of the geared rotary servo actuator 930. The rotary actuator 930 is, in turn, rigidly mounted to the cross plate using standoffs. The rotary actuator 930 is designed to apply out-of-plane rotation to test specimen 850.

The inner frame 932 is housed within and connected to the larger outer frame 922 by two shafts 905 and bearings. Each bearing is located near the lower apex of the outer frame 922. One of the shafts 905 extends through the outer frame 922 and is mechanically coupled to the shaft 924 of the geared rotary servo actuator 920. Rotary actuator 920, in turn, is rigidly fixed using standoffs. Rotation of the inner frame 932 and connected motor 920 provides for the in-plane rotation of the upper end 854 of the specimen 850.

In one embodiment, the overall coarse dimensions of the gimbal assembly 900 are 260 mm long, by 277 mm high, by 356 mm wide, with the majority of frame 924, 934 components fabricated from 12.7 mm thick aluminum plate to minimize mass and inertial effects. The total weight of the gimbal assembly 900 is, in one embodiment, approximately 7.7 kg including both rotary servo actuators 920, 930.

The shafts 905 between the outer 922 and inner 932 frames form a gimbal connection. The gimbal connection allows for the simultaneous application of both in-plane and out-of-plane rotary degrees of freedom. The gimbal style design also allows for simultaneous application of the required rotations about two orthogonal axes, which intersect at a single point in space. The single point is the point in space defined by the intersection of the imaginary line formed between the two horizontal shafts 905 and the imaginary line extending downward from the one vertical shaft 934. The upper end 854 of the coupled joint specimen 850 is connected to the gimbal assembly 900 at that imaginary point, and all motion and load inputs are applied via the gimbal assembly 900 and adjoining upper force sensor 824. This point may be referred to as the end effector or tool tip 849, and is the point of coincidence for two rotational axes.

As noted, the coupled joint test specimen 850 is physically located directly underneath the gimbal assembly 900. The upper end 854 of the specimen 850 is rigidly attached to the upper force sensor 824. At the same time, the lower end 852 of the specimen 850 is rigidly coupled to the top of the lower force sensor 822. The lower force sensor 822, in turn, is rigidly fixed to the lower test plate 816L.

As noted in connection with FIG. 8, the servo actuation system 830 also includes a linear servo actuator 910. This may be a commercially available actuator. The linear actuator 910 includes a servo motor preferably having a minimum peak thrust force and/or carrying capacity of about 2700 N. Again, this greatly exceeds loading values required for in vitro cervical spine testing; however, it is desired to have as much universality as possible built into the testing device 800.

The linear actuator 910 has a stroke length. Preferably, a stroke length having at least 300 mm of travel is provided. This is more than sufficient to replicate the proximal-distal end body displacements of the cervical spine during normal physiological motions. In the anterior-posterior (A-P) direction, 300 mm of travel is also more than sufficient for either a full flexion or a full extension motion. To ensure future utility such that a full flexion to full extension motion might be applied to larger multi-body lumbar test specimens, the A-P axis travel requirement may be doubled to 600 mm.

A 406XR linear positioning table 944 with a Gemini GV-U12E servo drive from Parker Automation of Irwin, Pa. may be chosen for the horizontal motion axis provided by actuator 910. The motion output for this device is provided via a moving carriage along the length of the actuator 910. In an alternate arrangement, a concentric moving shaft may be employed. The 406XR positioning table servo drive has 600 mm of linear travel. A 10 mm lead precision ground ball screw may be used with pre-tensioning of the screw assembly to eliminate backlash. The positioning table 944 is preferably made of extruded aluminum, making the table 944 light in weight for its size and load carrying capacity.

A vertical actuator is also provided as part of the actuation system 830. FIG. 8 shows vertical actuator 940 that is part of the servo actuation system 830. An example of a linear servo motor for actuator 940 is a model GSX-30 linear actuator provided by Exlar Corporation of Chanhassen, Minn. The model GSX-30 linear actuator along with model MPFLX-230/X35 servo amplifier by MTS Automation Division of New Ulm, Minn. may be used to comprise the vertical axis of motion. The MTS Automation servo amplifier has a velocity loop update rate of 100 µs. Unlike conventional ball or acme screw driven actuators, this device is driven by a planetary roller screw design. This design provides for greater contact area with the drive screw allowing for greater load carrying capacity and less wear over time. The roller screw design also permits small screw lead lengths as a standard feature. In one aspect, a lead length of 2.54 mm may be chosen to provide a large mechanical advantage for the vertical axis of motion.

The Exlar actuator 940 is mounted in a vertical orientation to the upper plates 814U, 816U of the triangular test frame 810. The actuator 940 has a co-centric shaft 942 extending through and below the plates 814U, 816U. The Parker 406XR actuator 910 is inverted and fixed to the moving end of the shaft 942 within the Exlar vertical servo actuator 940. The shaft 942 is connected to the horizontal translating carriage (not shown) of the table 944 in the horizontal servo actuator 910.

In one embodiment, the translation speeds provided to the end 854 of the specimen 850 by motors 910 and 940 during flexion and extension are up to 2.2 mm/s.

The following chart summarizes the motors useful for actuators 910, 920, 930 and 940. These motors are merely illustrative, and are not intended to imply any limitations to motors that might actually be employed in the testing systems of the present invention.

| Feature | Kollmorgen 9FG Geared Servomotor (920, 930) | Parker 406XR Linear Ball Screw Actuator (910) | Exlar GSX-30 Linear Roller Screw Actuator (940) |
|---|---|---|---|
| Range of Motion | 360° | 600 mm | 300 mm |
| Encoder Resolution | 0.0045° | 2 µm | 0.31 µm |
| Torque/Thrust | 10 Nm | 1780 N (Axial) 6227 N | 3560 N |
| Specific Feature | High torque-to-weight ratio | carrying capacity | Short screw lead, high resolution |

To protect the vertical actuator 940 from large, off-axis or shear loads, a parallel bearing rod is optionally provided within the frame structure 810. Preferably, two parallel bearing rods are placed on either side of the vertical actuator 940. FIG. 8 shows a pair of parallel bearing rods at 818. In one aspect, the rods 818 are spaced from the actuator 940 at about 190 mm. In one aspect, each rod 818 defines a hardened, precision shaft that is about 560 mm long and 25.4 mm in diameter. Such rods with matching shaft bearings (not seen) are available from Nook Industries, Inc. of Cleveland, Ohio. The individual bearings are able to accommodate up to 1° of shaft mal-alignment. The shaft bearings are pressed into custom-made aluminum flanged blocks 819, which are bolted to the upper cross plates 814U, 816U of the tri-clamping fixture frame 810. Additional coupling members 820 are designed and fabricated from aluminum alloy. These coupling members 820 serve to provide a unified sliding vertical actuator and bearing rod assembly to which the table 944 of the horizontal linear servo actuator 910 is mounted.

Vibrations from movement of table 944 and the motors 920, 930 within the gimbal assembly 900 may occur. To help eliminate or offset such vibrations, structural stiffening of the system 800 may be provided. An example is triangular stiffening plate 817 secured between shaft 942 and rods 818. In addition, a small amount of filtering of the final command signal 345 to the vertical motor 940 may be applied.

Figure 10:
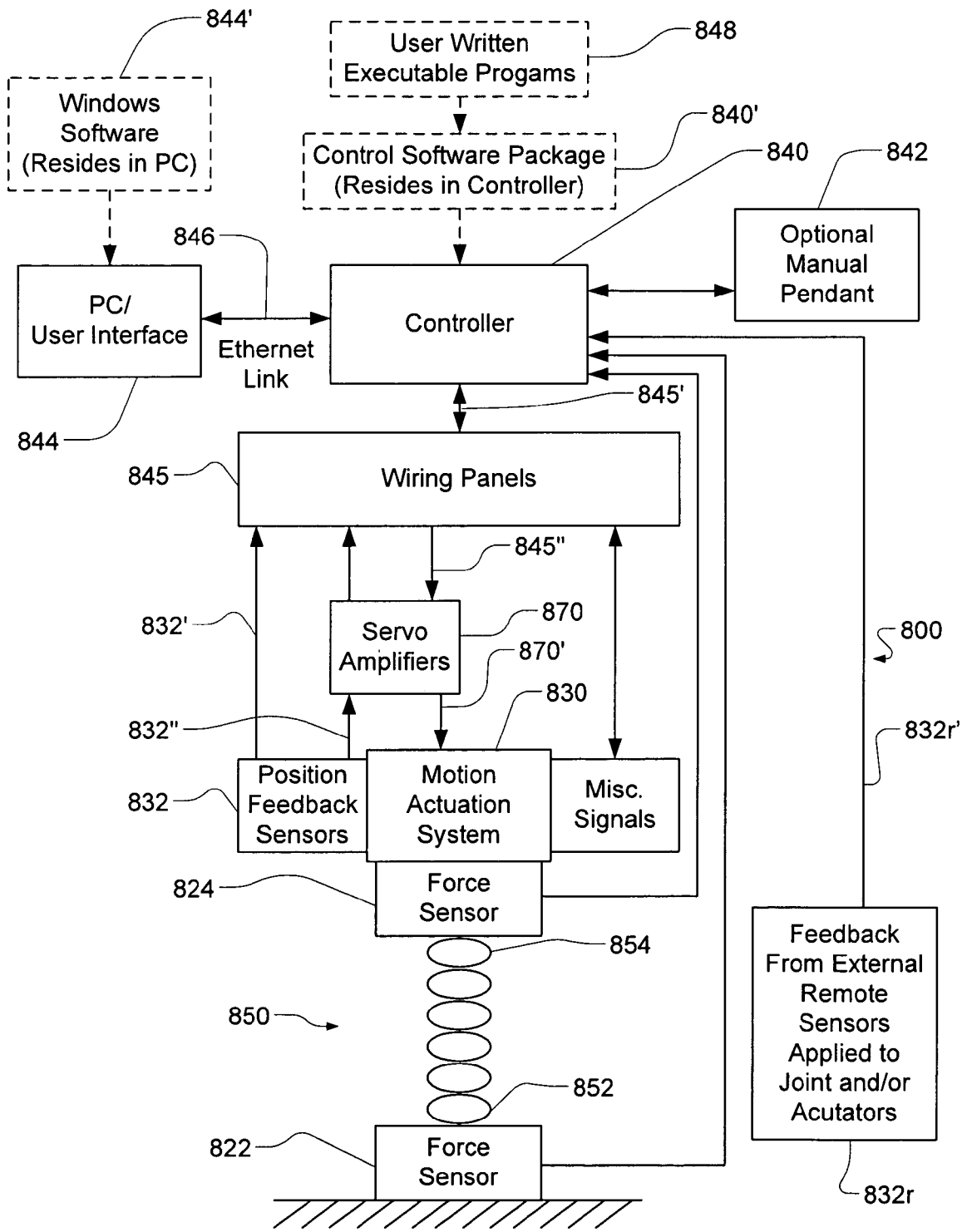
FIG. 10 is a schematic showing the testing system of FIG. 8.

As noted, FIG. 10 shows a controller 840. The controller 840 defines a computer having control software loaded thereon. The controller 840 operates to selectively control the motion of the actuators 910, 920, 930, 940. In one aspect, the controller 840 is a model MV540 six-axis controller available from Adept Technologies of San Jose, Calif. The controller 840 may include digital signal processing (DSP) boards that are compatible with, and slotted into, a VME back plane architecture. The VME architecture defines a bus that allows cards to communicate with each other. In one aspect, each DSP board has a maximum sampling rate of 1,000 Hz and provides for sensor signal filtering and zeroing. The VME architecture imbues functionality to the controller 840 and allows it to be tailored to different applications. The controller 840 may command up to six independent servo driven axes simultaneously.

As noted, the robotic controller 840 is operated through control programs. In one aspect, the control program is written in the Adept V+ command language. The V+ command language is similar in structure and form to other computer languages such as Basic and Fortran. A V+ command library is commercially available which possesses many individual commands tailored to robotic control. The controller 840 also includes various software and hardware features such as a library of utility software programs, a multi-tasking programming environment, serial and digital signal I/O capability, and an operator's panel with emergency stops.

Optionally, the testing system 800 includes a hand-held pendant. A pendant is shown in FIG. 8 at 842. The pendant serves as an alternative manual control device for moving the upper end 854 of the specimen 850. The user may also use the pendant 842 as a device for teaching the controller 840 a path of movement.

To better understand the control features of the system 800, a more detailed operational schematic is provided. FIG. 10 presents a schematic showing the interrelationship of various parts of the system 800 as connected to the controller 840. First, the coupled joint specimen 850 is shown schematically. The specimen 850 again has a lower end 852 that is translationally and rotationally fixed. The specimen 850 also has an upper end 854 that is translationally and rotationally controlled. Movement of the upper end 854 is controlled by the controller 840. In addition, forces (including torque) applied to the test specimen 850 are controlled by the controller 840 through the actuation system 830. The actuation system 830, again, preferably includes various servo motors 910, 920, 930, 940 for inducing motion to the upper end 854 of the specimen 850.

The controller 840 interacts with a computer 844. Preferably, the computer is a personal computer, or "PC," shown at 840 having a commercially available operating system. The personal computer operates existing software programs 844'. In one embodiment, an Adept™ Windows™ software package is downloaded onto the PC 844 to provide communication with the servo actuators 910, 920, 930, 940. The Adept Windows Software is shown at 844', and resides on the PC 844. The Adept PC windows environment provided on the PC 844 serves as a means of communication with the controller 840 as well as an editor for the creation of custom control programs.

Communications between the controller 840 and the computer 844 are provided. Preferably this is through an Ethernet link 846. The Ethernet link 846 provides for the exchange of data files and software programs between the controller 840 and the hard drive of the PC 844 in real time.

Utility software programs for operating the controller 840 are also employed. Such utility programs are shown schematically at 840', and reside on the controller 840. Such utility programs may also be provided as a commercially available control software package from Adept Technologies. The Adept software allows the user to create and store custom user-written control programs 848 for the controller 840. In this way, the controller 840 loads and executes control programs that are written by the user.

The Adept control software 840' also includes operational software. The operational software includes a specification program that allows the user to custom-input various setup parameters specific to the user's actuator equipment. The software also allows the user to input "tuning" parameters which define the closed loop control performance of the system 300 or 800.

The Adept software package 840' further includes a utility program that serves as a kinematic device module. The utility software tells the controller 840 the kinematic configuration of the system 800. In the case of system 800, the kinematic configuration is defined by the number and types of axes and their relation to each other. In one aspect the kinematic device module may describe an overhead or gantry type actuation system having up to six different movable axes comprised of up to three linear axes along three orthogonal directions for imparting linear motions and/or forces, and up to three rotational axes disposed below the linear axes for imparting rotational motions and/or forces.

Returning to FIG. 10, at both the upper 854 and lower 852 ends is a corresponding force sensor 822 and 824. The force sensors 822, 824 provide feedback to the electronic digital signal processing boards residing in the Adept controller 840. The controller 840 receives and monitors the sensory feedback and input signals from the force sensors 822, 824.

FIG. 10 shows the actuation system 830 above the upper force sensor 824. As noted, the actuation system 830 includes motion actuators that drive the upper end 852 of the test specimen 850. The actuation system 830 includes the actuators 910, 920, 930 and 940 described above. The actuators 910, 920, 930, 940 are preferably servo driven motors that provide linear or rotary motion output as commanded.

Each of the servo actuators 910, 920, 930, 940 includes one or more position feedback sensors 832. Preferably, the position feedback sensors 832 are high resolution encoders. An encoder is an electromechanical device that converts linear or rotary displacement into digital or pulse signals. The encoder may be an optical encoder which consists of a disk mounted on a rotating shaft. The disk has patterns of opaque and transparent sectors coded into the disk. The encoder also has a light source and a photo detector, or light sensor on opposing sides of the disk. As the disk rotates, the patterns coded onto the disk interrupt the light emitted onto the photo detector. A digital or pulse signal output is thus generated in response. The encoder provides precise position feedback to the controller 840.

Other types of encoders may be employed. These may include a serial absolute encoder or a sinusoidal encoder. In addition, other types of position feedback sensors 832 may be used. Examples include resolvers and potentiometers. An external remote sensor 832r may alternatively be used. The external remote sensor 832r may operate through optics or other processes. A signal 832r' is then sent from the external remote sensor 832r to the controller 840 to inform the controller 840 as to the position of the specimen 850 or actuators 910, 920, 930, 940.

In one aspect, the position feedback sensors 832 define incremental encoders that send pulse signals back to the controller 840. The pulse signals are denoted in FIG. 10 as output signals 832' and 832". Output signals 832' connect directly to the controller 840 through wiring panels 845. Output signals 832", on the other hand, first connect to the servo amplifier 870 and are then directed from the servo amplifier 870 to the controller 840.

It is noted that either form of output signal 832' or 832" may be employed in the testing system 800. In the embodiment shown in FIG. 10, both forms of output signals 832', 832" are employed. In any instance, the output signals 832', 832" are received by the controller 840 and processed to determine the current position, direction of travel, and speed of the respective servo actuators 910, 920, 930, 940 within the motion actuation system 830.

In operation, the controller 840 and its resident operational and utility software 840' control each of the servo actuators 910, 920, 930, 940. Command signals 845' are sent from the controller 840 and to the wiring panel 845. From there, analog motion and velocity commands 845" are directed to the servo amplifiers 870. The servo amplifiers 870 receive the analog motion and/or velocity commands 845" and convert them to electrical voltage and current outputs 870' as necessary to drive the servo actuators 910, 920, 930, 940. The result is that the signals 845', 845" and 870' are used for control and coordinated motion of the robotic testing system 800.

The testing system 800 is specially programmed to selectively move and rotate the upper end 854 of the spinal test specimen 850 about a moving point of rotation within a selected plane. In robotic terms, the moving point of rotation may be referred to as the tool tip location 849, which is user defined. Stated more broadly, the controller 850 selectively directs command signals 845', 845", 870' to the actuation system 830 in order to simultaneously apply selected forces and motions to the moving end 854 of the coupled joint 850, and for selectively rotating the moving end 854 of the coupled joint 850 about a moving center of rotation within a selected plane.

In order to orient the controller 840, a calibration process may be used after the computer 844 is booted up. This defines a location for the tool tip 849 from which all subsequent motion may be referenced. For in vitro testing it is not necessary for the tool tip 849 to be located a particular distance from any jig, fixture or conveyor, as might be the case for an assembly robot. What matters is that the tool tip 849 is secured to the upper end 854 of the specimen 850. Using the SPEC.V2 program of the Adept software package 840', this initial position parameter was set to "calibrate to current position." This means that wherever the tool tip 849 is physically located at system 800 boot-up becomes a "World Cartesian Coordinate System" (or "WCS") origin. As noted, the physical location of the actuation system 830 is defined as the location of the configured tool tip 849, which in one aspect may be the intersection point of the two imaginary gimbal axes and in another aspect may be any user defined location with respect to the intersection point of the two imaginary axes.

It is important to have the axes for the upper force sensor 824, e.g., a JR3 load cell, aligned with the WCS axes for two reasons. First, horizontal alignment of the load cell face (and hence the vertical alignment of the load cell z-axis per FIG. 1) allows for the physical mounting of the spinal test specimen 850 in an upright and neutral orientation. Second, the WCS directional axes needed to correspond to those of the upper force sensor 824 so that the appropriate WCS axes can respond to force component readings under load control scenarios. Alignment of the load cell axes with the WCS axes is achieved by adjusting the gimbal orientations manually prior to system 800 start up.

The above alignment and calibration procedures are preferably performed each time the testing system 800 is used. Default values for translation and rotation about the "x," "y," and "z" axes assigned by the controller 840 for the start position of the tool tip 849 are 0 mm, 0 mm, 0 mm, 0°, 180° and 180°, respectively. Once the computer 844 is booted to start the system 800, these default values are in place.

Before readings are taken from either of the JR3 force sensors 822, 824, it is first desirable to initialize, zero, and specify the preferred units with respect to force and distance. These steps may be performed in one aspect by using the 'FORCE.MODE', and the 'FORCE.OFFSET' commands as outlined in the Adept Force VME User's Guide. The international system of units (SI) of force and displacement may be selected for all tests conducted using the system 800.

Once initialized, the force sensor coordinate reference frame is by default located with its origin in the geometrical center of the upper force sensor 824, and with the z axis aligned concentric within the center line of the cylindrically shaped force sensor 824. This properly positions and orients the orthogonal force reference system about which all sensor force and moment readings are reported. For the spinal implant testing, it is often desirable to read all force and moment data at the exact point of applied global motion and load input to the upper end 854 of the specimen 850. As outlined previously, this point is typically defined by the intersection of the two rotational axes of the gimbal assembly 900. Since the upper JR3 force sensor 824 is mounted concentrically with the second gimbal rotational axis (the axis defined by the shaft 942), the transformation required to relocate the default sensor coordinate system to this point was a z-axis displacement of 51.54 mm. The spatial orientation of the default sensor coordinate system with respect to the sensor was maintained i.e. no rotational transformations were applied.

It is noted that there are essentially two reference frames on boot up: one to define the robot tool tip location point and origin, and another to define the point and directions in space about which the load sensor 824 reports all applied forces and moments. At boot up, these two reference frames may not be in the same place. It is desirable that the load sensors report forces and moments seen at the tool tip. This may be done by moving or relocating the force sensors coordinate system from its initial or default location to lay coincident with the tool tip location. Once that is done, forces and moments reported by the load cell represent those occurring at the tool tip.

For some forms of testing, it is desirable to move the tool tip or motion application point to a location other than the intersection of the gimbal axes. In these cases it is usually desirable to move the force reference frame to the new tool tip location as well so that the system is still reading forces and moments about the point of motion/force application. The force reference frame transformation may thus be implemented using the 'FORCE.FRAME' command of the control software package 840'. The user may report force and moment readings about a different reference frame located at some other point of interest. In this respect, a user-defined force reference frame transformation may be specified and commanded.

It is noted that the controller 840 using Adept control software 840' is inherently a position control device. This enables the programming of all motion input parameters. In the context of cervical spine testing, replication of sagital plane spinal movements using the controller 840 may require formulation of simultaneous motion commands for the three degrees of freedom involved. Those are:

(1) in-plane rotation 420, which corresponds to rotation within the sagital plane about the flexion-extension axis "y" in FIG. 1;

(2) horizontal translation 415, which correlates to movement along the forward axis "x" in FIG. 1; and (3) vertical translation 410, which correlates to movement along the vertical axis "z" from FIG. 1.

Sagittal plane global rotation was defined as an independent variable programmed to increase at a constant rotational velocity. The corresponding "x" and "z" axis positions were defined as:

$$X = A\theta^2 + B\theta$$

$$Z = C\theta^2 + D\theta$$

Where: X=programmed actuation system x-axis translation (mm)

Z=programmed actuation system z axis translation (mm)

$\theta$=global flexion-extension angle (degrees)

A, B, C, D=user-specified constant coefficients.

Figure 11B:
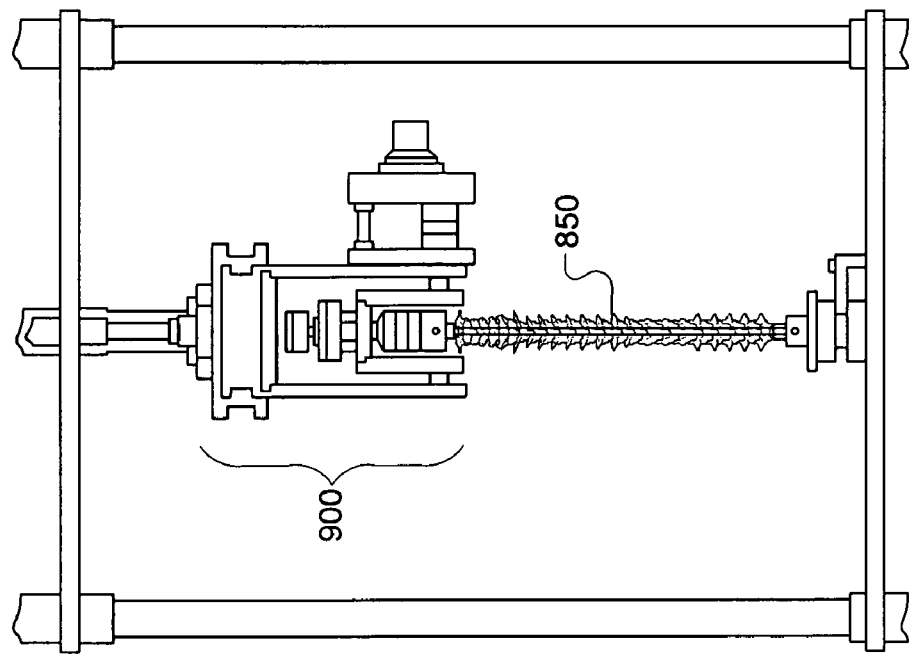
FIG. 11B is a front view of the coupled joint testing system of FIG. 8. Here, the spine specimen remains in a vertical position to accommodate flexion and extension testing.
Figure 11A:
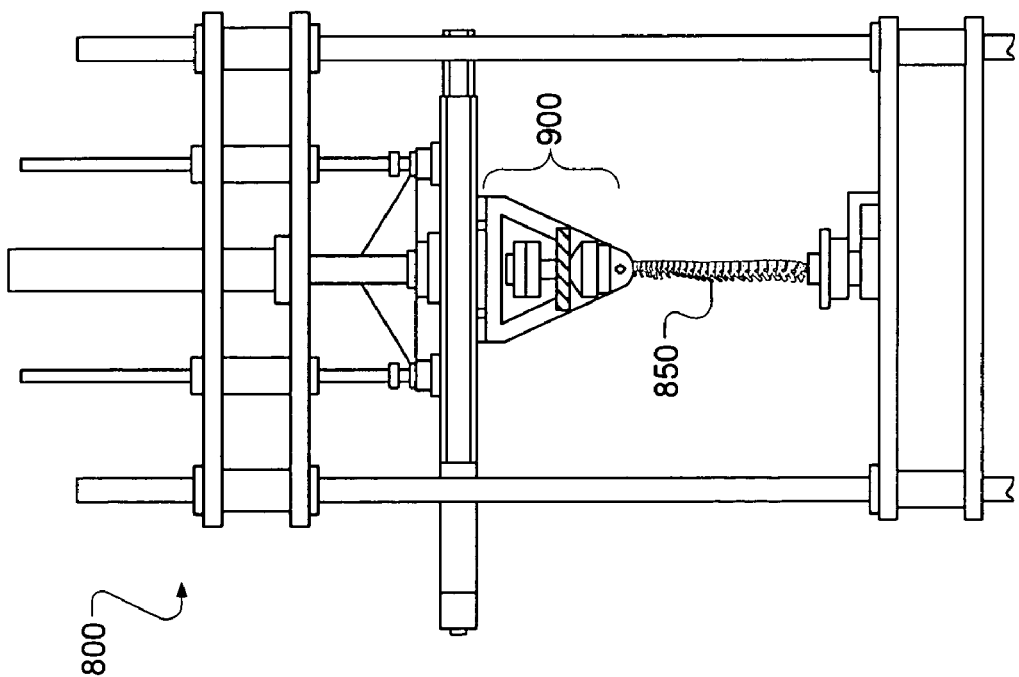
FIG. 11A is a side view of the coupled joint testing system of FIG. 8. Here, the spine specimen is in a vertical position to accommodate flexion and extension testing.

FIG. 11A is a side view of the coupled joint testing system 800 of FIG. 8. Here, the spine specimen 850 is in a frontal position to accommodate flexion and extension testing. It can be seen that the spinal specimen 850 is physically located directly underneath the rotary servo actuators 920, 930 and associated gimbal frames 922, 932. The upper end 854 of the specimen 850 is rigidly attached to the upper force sensor 824, while the lower end 852 is rigidly coupled to the top of the lower force sensor 822. The lower force sensor 822 is, in turn, rigidly fixed to the lower support plate 816L.

All motion and load inputs from the actuation system 830 are applied to the coupled joint 850 via the gimbal assembly 900 and upper force sensor 824. The upper force sensor 824 moves with the tool tip 849, while the lower load sensor 822 remains stationary.

As noted previously, the controller is programmed to control force. In order to control force, the originally programmed path comprised of $\theta$ rotations, and x and z translations is modified according to user-defined/programmed force criteria. This is done in real time as the actuators are moving so as to maintain target end loads on the test specimen throughout its range of motion. Control of force in this manner is via commanded changes of position. Other ways may be used to achieve force control. For example, the user may control the velocities of specific actuators involved in applying those loads.

FIG. 11B is a front view of a portion of the coupled joint testing system of FIG. 8. The system 800 has been enlarged to show the gimbal assembly 900. Here, the spine specimen 850 remains in a frontal position to accommodate flexion and extension testing. The testing system 800 has not been actuated in either FIG. 11A or FIG. 11B to move the tool tip 849 and connected moving end 854 of the specimen 850.

Figure 12B:
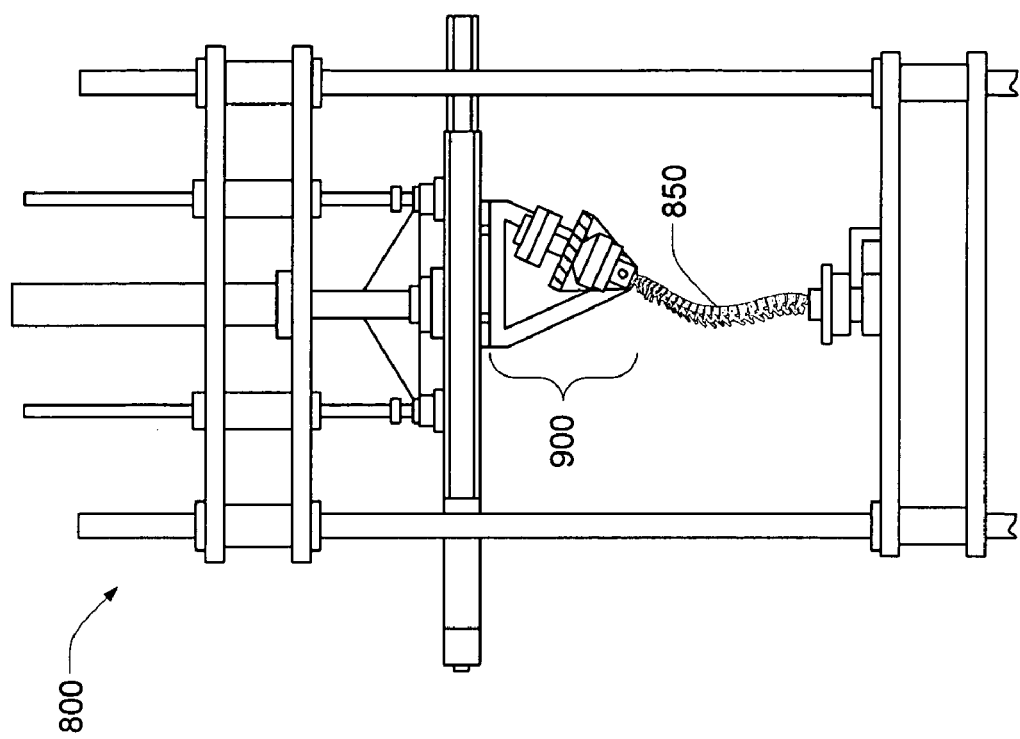
FIG. 12B is another side view of the coupled joint testing system. Here, the spine specimen is undergoing flexion.
Figure 12A:
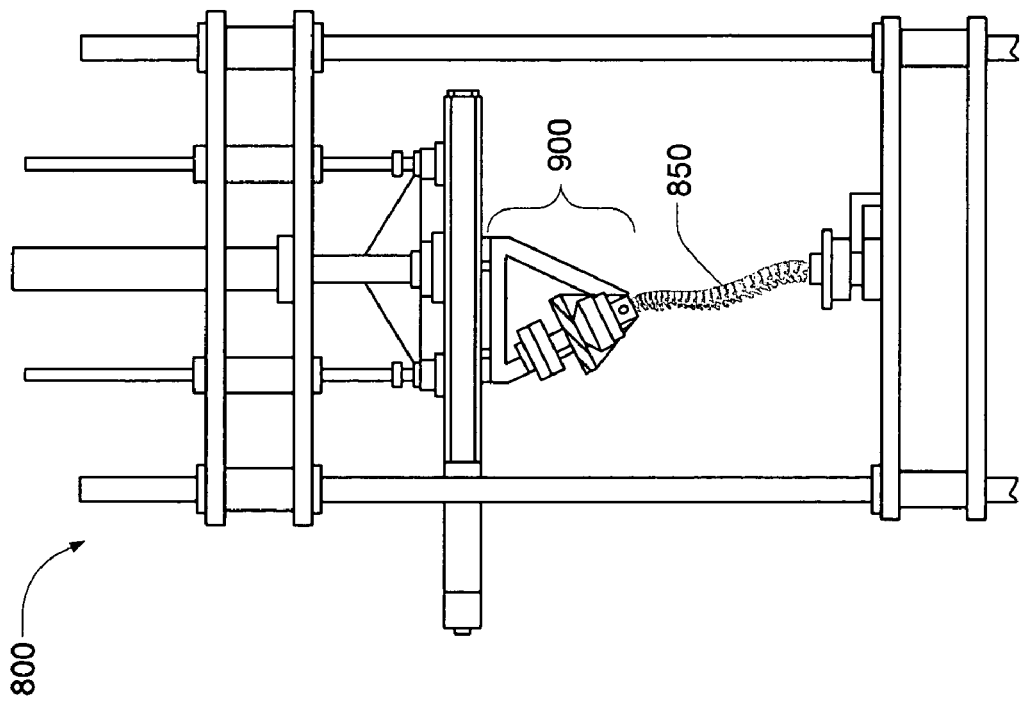
FIG. 12A is another side view of the coupled joint testing system of FIG. 8. Here, the spine specimen is undergoing extension.

FIG. 12A is another side view of the coupled joint testing system 800 of FIG. 8. Here, the system 800 has been activated, and the spine specimen 850 is undergoing extension.

FIG. 12B is another side view of the coupled joint testing system 800. Here, the spine specimen 850 is undergoing flexion. It is understood that in testing, the specimen 850 may be moved through flexion and extension cycles repetitively.

Further, in accordance with the unique features of the system 800, in-plane and out-of-plane rotation may be applied to the upper end 854 of the specimen 850 simultaneously. Still further, the amount of force, motion and the rate of motion may be controlled through the controller 840 of FIG. 10. Further still, the point at which all motions and loads are applied to the specimen (by moving the tool tip location), and the point at which all forces and moment are measured and recorded (by moving the force reference frame) may be varied according to user preference.

Figure 12C:
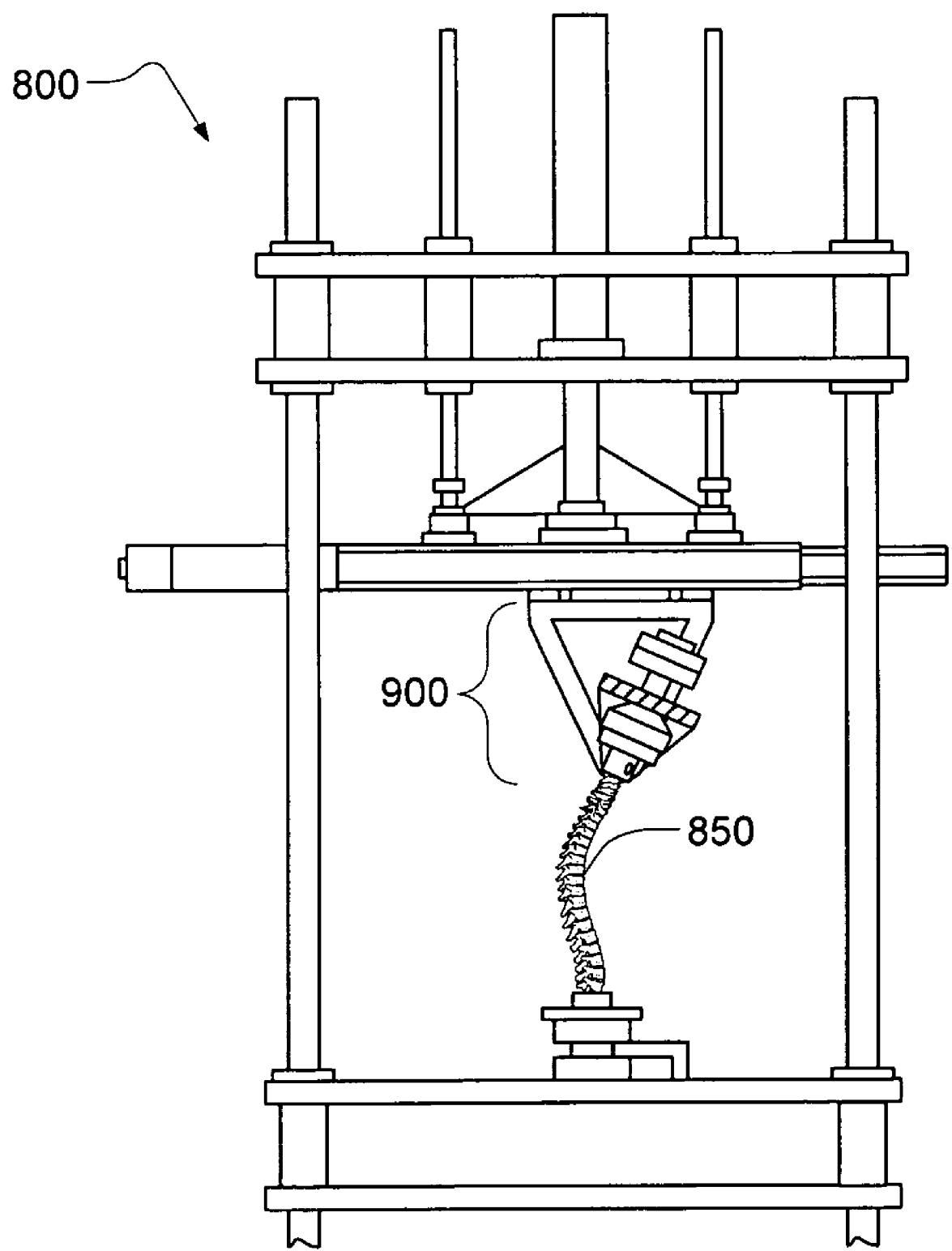
FIG. 12C is another side view of the coupled joint testing system. Here, the spine specimen is undergoing both flexion and axial rotation.

FIG. 12C is another side view of the coupled joint testing system 800. Here, the spine specimen 850 is undergoing both flexion and axial rotation. Thus, a fourth degree of freedom is demonstrated.

It is noted that a large amount of hardware for the servo actuators 910, 920 and 930 and gimbal assembly 900 is supported by the shaft 942 of the vertical servo actuator 940. In one embodiment, the total weight of all of the servo hardware that is suspended from the shaft 942 is 490 N. When power is removed from the servomotor for the vertical actuator 940, potential exists for the equipment associated with the servo actuators 910, 920, 930 to fall from the elevated working position due to gravitational forces. Such a condition might occur when the controller 840 is instructed to turn off high power (i.e., active closed-loop control of the servomotors no longer in effect), when an emergency stop button (not shown) is pressed, or when the entire servo actuation system 830 is powered off. Therefore, an optional braking system 860 may be designed to maintain the position of the vertical shaft 942 when the testing system 800 is not under active control.

In one embodiment, the braking system 860 uses counterbalanced mass and a rotary friction disc brake to counter the weight of the servo actuators 910, 920, 930 and other hardware suspended from the vertical actuator shaft 942. In the embodiment shown in FIG. 8, two aluminum tubes 862 are positioned above the upper stabilizing plate 814U. Each tube 862 is about 51 mm in diameter. The tubes 862 respectively suspend a different pulley 864(1), 864(2). The first pulley 864(1) is mounted on a plain bearing, and is coupled to the shaft of a brake (not shown). Preferably, the brake is a model FSB050 rotary friction disc brake. The disc brake is available from Inertia Dynamics of Collinsville, Conn., and has a holding torque capacity of 5.6 Nm when powered off. With application of power to the brake, an internal solenoid switch releases the friction disc, thereby allowing the shaft to rotate freely. The attached pulley inner diameter was 33 mm, allowing a single brake to resist approximately 340 N of cable tension around the pulley 864(1).

The second pulley 864(2) is an idler pulley. The idler pulley 864(2) is horizontally offset from the braked pulley 864(1) and mounted on a plain bearing. The idler pulley 864(2) is always able to rotate freely.

Threaded blind holes are drilled into the upper end face of each bearing rod 818. Threaded steel eyes (not seen) are then fastened into each blind hole. A pre-stretched nylon coated cable 866 with 1120 N rated braking strength may be attached to each eye. The cable 866 is wound around each braking pulley three times and then fed over the top of the idler pulley 864(2) and down. Dead weights 868 are attached to the terminal end of the cables 866. The dead weights 868 maintain sufficient back tension in the cables 866 for the braking system 860 to work properly.

The Adept controller 840 is preferably hardwired to the braking system 860 through controller electrical panels (not shown). This allows the controller 840 to selectively engage or disengage the disc brake on the braking pulley 864(1).

Figure 13:
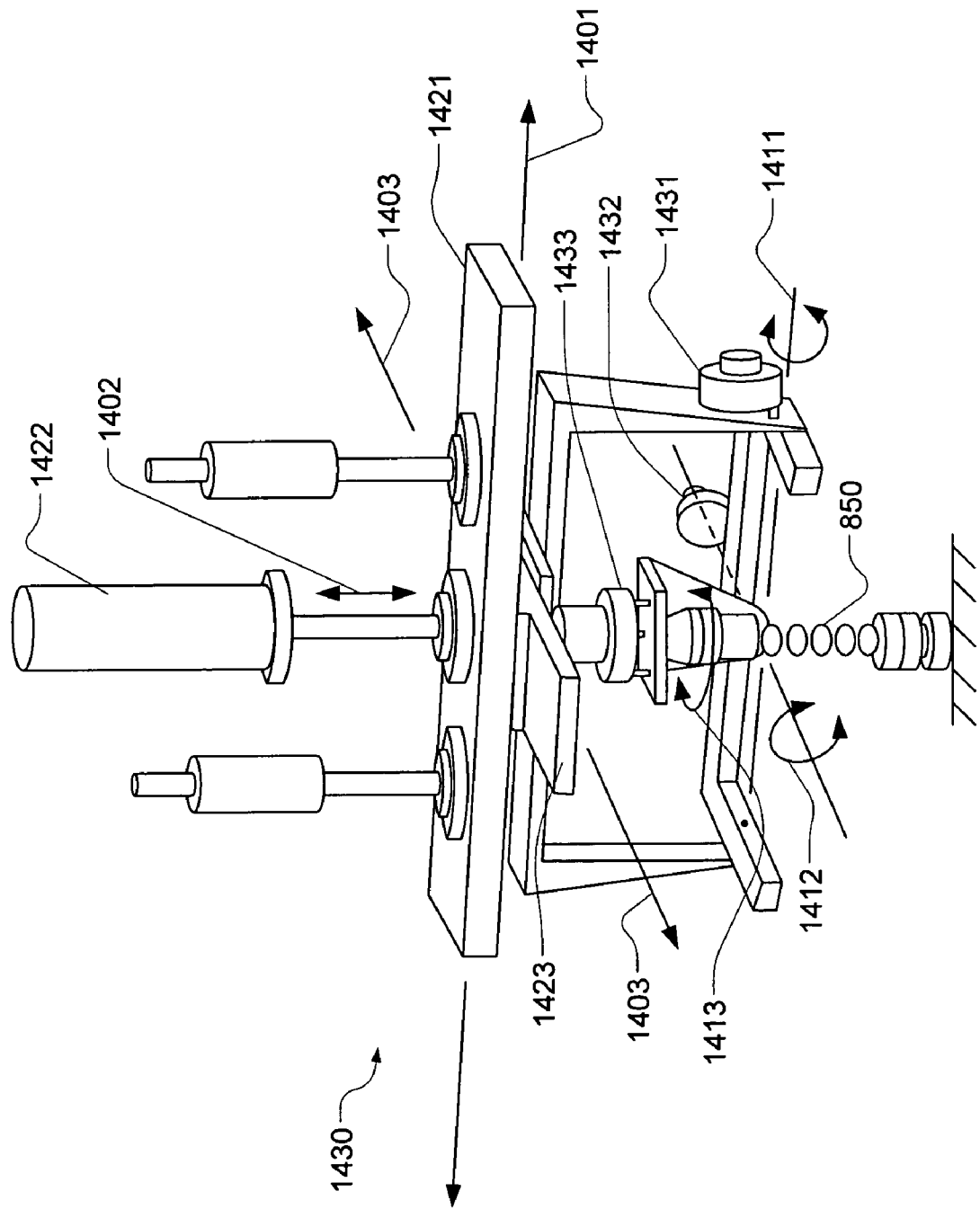
FIG. 13 is a perspective view of a servo actuation system in an alternate embodiment. In this embodiment, six degrees of freedom are provided.

As noted above, the coupled joint testing system 800 may be adapted to provide motions and forces in six degrees of freedom. FIG. 13 is a perspective view of a servo actuation system 1430 in an alternate embodiment. In this embodiment, six degrees of freedom are provided for moving an upper end 854 of a spinal specimen 850. The six degrees of freedom are shown according to the following arrows:

a first translational degree of freedom 1401 along a first translational axis;

a second translational degree of freedom 1402 along a second translational axis, the first and second translational axes forming a first plane of motion;

a third translational degree of freedom 1403 along a third translational axis, the second and third translational axes forming a second plane of motion;

a first rotational degree of freedom 1411 about a first rotational axis that lies within the first plane of motion and is parallel to the first translational axis;

a second rotational degree of freedom 1412 about a second rotational axis orthogonal to the first rotational axis and moves within the second plane of motion; and a third rotational degree of freedom 1413 about a third rotational axis orthogonal to the second rotational axes and moves within a plane orthogonal to the second rotational axis.

It may generally be stated that the actuation system 1430 has six degrees of freedom comprising three substantially orthogonal axes in a Cartesian coordinate system, and three rotational axes which rotate about a respective orthogonal axis. Preferably, the actuation system 1430 is a control actuation system. The actuation system 1430 is operatively connected to the moving end of a coupled joint for imparting the six degrees of freedom.

In the illustrated arrangement of FIG. 13, the first translational degree of freedom originates along a first horizontal axis 1401; the second translational degree of freedom originates along a second vertical axis 1402; and the third translational degree of freedom originates along a third horizontal axis 1403 and is orthogonal to the first horizontal axis 1402. The first and second axes form a first plane of motion, while the second 1402 and third 1403 horizontal axes form a second plane of motion.

In the illustrated arrangement of FIG. 13, the first rotational degree of freedom is about the first rotational axis 1411 and is within the first plane of motion and parallel to the first horizontal axis 1401; the second rotational degree of freedom is about the second rotational axis and is orthogonal to the first rotational axis and moves within the second plane of motion; and the third rotational degree of freedom is about the third rotational axis, is orthogonal to the second rotational axis and moves within a plane orthogonal to the second rotational axis.

In order to drive the specimen 850 according to the six degrees of freedom, the following corresponding actuators are provided:

a first translational actuator 1421 for moving the specimen 850 along the first translational axis;

a second translational actuator 1422 for moving the specimen 850 along the second translational axis;

a third translational actuator 1423 for moving the specimen 850 along the third translational axis;

a first rotational actuator 1431 for moving the specimen 850 about the first rotational axis;

a second rotational actuator 1432 for moving the specimen 850 about the second rotational axis; and a third rotational actuator 1433 for moving the specimen 850 about the third rotational axis.

It is noted that the actuator system 1430 providing six degrees of freedom is only one possible configuration. Different mechanical configurations may be employed with different sequences or orders of rotations to achieve the same end position of the specimen 850. This could result in a change in the description of the rotational axes. Thus, for example, the first rotational degree of freedom may be orthogonal to the first rotational axis and move within the second plane of motion, while the second rotational degree of freedom may lie within the first plane of motion and be parallel to the first horizontal axis.

It is also understood herein that the disclosed methods and systems are not limited to the testing of medical products. The methods and systems are presented in the context of medical device testing, but have utility and novelty in any context in which implants are provided for coupled joints. Also, while it will be apparent that the invention herein described is well calculated to achieve the benefits and advantages set forth above, it will be appreciated that the invention is susceptible to modification, variation and change without departing from the spirit thereof.

Certain features of the present invention are described in terms of a set of numerical values. It should be appreciated that values and ranges formed by numerical references are merely illustrative, and should not be construed as limitations to the inventions, where are defined by the claims below. Although some of the dependent claims have single dependencies in accordance with U.S. practice, each of the features in any of such dependent claims can be combined with each of the features of one or more of the other dependent claims dependent upon the same independent claim or claims.

We claim:

1. A system for testing a coupled joint for a physiological structure, the coupled joint mounted within the system to have a fixed end and a moving end, comprising:
    an actuation system operatively connected to the moving end of the coupled joint for imparting at least four degrees of freedom, the four degrees of freedom comprising a first translational degree of freedom along a first translational axis, a second translational degree of freedom along a second translational axis, the first and second translational axes forming a first plane of motion, a first rotational degree of freedom about a first rotational axis orthogonal to the first plane of motion, and a second rotational degree of freedom about a second rotational axis orthogonal to the first rotational axis and moving within the first plane of motion;
    a first force sensor disposed between the actuation system and the moving end of the coupled joint for sensing applied force; and
    a controller for applying selected forces, motions, or combinations thereof, to the moving end of the coupled joint within the four degrees of freedom so as to simulate movement of the physiological structure, forces on the physiological structure, or both.

2. The system of claim 1, wherein the controller receives input signals in order to apply the selected forces, motions, or combinations thereof to the moving end of the coupled joint within the four degrees of freedom.

3. The system of claim 2, further comprising a second force sensor disposed at the fixed end of the coupled joint for sensing transmitted force.

4. The system of claim 3, wherein the input signals to the controller comprise force signals sent from the first force sensor and the second force sensor.

5. The system of claim 3, wherein the input signals to the controller comprise motion signals.

6. The system of claim 5, wherein the motion signals to the controller comprise at least one of velocity and position.

7. The system of claim 6, wherein the motion signals to the controller are sent from encoders.

8. The system of claim 3, wherein the input signals to the controller comprise at least one of pressure, force or strain signals from a sensor affixed to the coupled joint.

9. The system of claim 4, wherein the two translational degrees of freedom comprise a first degree of freedom along a first horizontal axis, and a second degree of freedom along a second vertical axis.

10. The system of claim 4, wherein the controller, the input signals, and the actuation system are part of a control system.

11. The system of claim 5, wherein the actuation system is a servo system, a stepper motor system, a hydraulic system, a pneumatic system, or a magnetically driven system.

12. The system of claim 2, wherein the input signals are sent in response to at least one of pressure, force, motion, strain and pressure.

13. The system of claim 6, wherein the actuation system comprises:
    a first rotary actuator for imparting rotation to the coupled joint about the first, rotational axis; and
    a second rotary actuator for imparting rotation to the coupled joint about the second rotational axis.

14. The system of claim 13, wherein the first and second rotary actuators operatively interact orthogonally through a gimbal connection.

15. The system of claim 14, wherein the first and second rotary actuators provide rotation up to at least 180°.

16. The system of claim 13, wherein the actuation system further comprises:
    a first linear actuator for imparting translation to the coupled joint along the first horizontal axis; and
    a second linear actuator for imparting translation to the coupled joint along the second vertical axis.

17. The system of claim 16, wherein the first linear actuator and the second linear actuator each provide travel of about 200 mm to about 700 mm.

18. The system of claim 2, wherein the coupled joint is a spinal specimen comprising at least one spinal motion segment unit.

19. The system of claim 18, wherein the spinal specimen comprises at least a portion of a cervical spine, a thoracic spine, a lumbar spine, or combinations thereof.

20. The system of claim 18, wherein the spinal motion segment unit is either a model or a cadaveric sample.

21. The system of claim 18, wherein the spinal specimen further comprises a spinal implant.

22. The system of claim 4, wherein the first and second force sensors each define a six-axis sensor.

23. The system of claim 3, wherein:
    the testing system further comprises a frame for supporting the coupled joint, with the frame defining a volume for receiving the coupled joint; and
    the testing system volume is capable of receiving coupled joints of varying lengths.

24. The system of claim 23, wherein:
    the coupled joint is supported within the frame in a vertical orientation; and
    the system further comprises a lower clamping fixture for releasably supporting the fixed end of the coupled joint, and an upper clamping fixture for releasably supporting the moving end of the coupled joint.

25. The system of claim 2, wherein the first translational degree of freedom originates along a first horizontal axis, and the second translational degree of freedom originates along a second vertical axis.

26. The system of claim 25, wherein the actuation system imparts six degrees of freedom to the moving end of the coupled joint, the six degrees of freedom comprising:
the first translational degree of freedom originating along a first horizontal axis, and the second translational degree of freedom originating along a second vertical axis, the first horizontal axis and the second vertical axis defining the first plane of motion;
a third translational degree of freedom originating along a third horizontal axis orthogonal to the first horizontal axis, the second and third translational axes forming a second plane of motion;
the first rotational degree of freedom residing about a first rotational axis that lies within the first plane of motion and is parallel to the first horizontal axis;
the second rotational degree of freedom residing about the second rotational axis that is orthogonal to the first rotational axis and moves within the second plane of motion; and
a third rotational degree of freedom about the third rotational axis orthogonal to the second rotational axis and moving within a plane orthogonal to the second rotational axis.

27. A system for testing a coupled joint for a physiological structure, the coupled joint mounted within the system to have a fixed end and a moving end, comprising:
a control actuation system operatively connected to the moving end of the coupled joint for imparting at least four degrees of freedom;
a first force sensor disposed between the actuation system and the moving end of the coupled joint for sensing applied force;
a second force sensor disposed at the fixed end of the coupled joint for sensing transmitted force; and
a controller for selectively directing input signals to the control actuation system in order to simultaneously apply selected forces and motions to the moving end of the coupled joint that correlates to a human physiologic condition.

28. A system for testing a medical device for a human musculoskeletal structure, the musculoskeletal structure mounted within the system to have a fixed end and a moving end and having the medical device connected thereto, the system comprising:
a control actuation system operatively connected to the moving end of the musculoskeletal structure for imparting six degrees of freedom, the six degrees of freedom comprising three substantially orthogonal translation axes in a Cartesian coordinate system, and three rotational axes;
a first force sensor disposed between the control actuation system and the moving end of the musculoskeletal structure for sensing applied force; and
a controller for selectively directing input signals to the control actuation system in order to apply selected forces, motions, or combinations thereof, to the moving end of the musculoskeletal structure within the six degrees of freedom to simulate a physiological condition.

29. The system of claim 28, wherein:
the three orthogonal translation axes comprise a first translational degree of freedom along a first translational axis, a second translational degree of freedom along a second translational axis, and a third translational degree of freedom along a third translational axis;
a first plane of motion is formed by the first and second translational axes;
a second plane of motion is formed by the second and third translational axes; and
the three rotational axes comprise a first rotational degree of freedom about the first translational axis, a second rotational degree of freedom about the second translational axis, and a third rotational degree of freedom about the third translational axis.

30. The system of claim 29, wherein:
the first translational axis and the third translational axis are each substantially horizontal;
the second translational axis is substantially vertical;
the first rotational degree of freedom resides about a first rotational axis that lies within the first plane of motion and is parallel to the first horizontal axis;
the second rotational degree of freedom resides about the second rotational axis and is orthogonal to the first rotational axis and moves within the second plane of motion; and
the third rotational degree of freedom resides about the third rotational axis orthogonal to the second rotational axis and moves within a plane orthogonal to the second rotational axis.

31. The system of claim 29, wherein:
the first translational axis and the third translational axis are each substantially horizontal;
the second translational axis is substantially vertical;
the first rotational degree of freedom resides about the second rotational axis and is orthogonal to the first rotational axis And moves within the second plane of motion;
the second rotational degree of freedom resides about a first rotational axis that lies within the first plane of motion and is parallel to the first horizontal axis; and
the third rotational degree of freedom resides about the third rotational axis orthogonal to the second rotational axis and moves within a plane orthogonal to the second rotational axis.

32. The system of claim 28, further comprising:
a second force sensor disposed at the fixed end of the musculoskeletal structure for sensing transmitted force.

33. The system of claim 32, wherein the musculoskeletal structure is a vertebral structure.

34. The system of claim 32, wherein the musculoskeletal structure:
is a cadaveric sample, a biofedilic model, or an artificial model; and
defines at least three vertebrae.

35. The system of claim 1, wherein the physiological structure is a human cadaveric sample, a biofidelic model, or an artificial model.

36. The system of claim 27, wherein the physiological structure is a human cadaveric sample, a biofidelic model, or an artificial model.

* * * * *